(12) United States Patent
Götz et al.

(10) Patent No.: US 11,020,441 B2
(45) Date of Patent: Jun. 1, 2021

(54) PROBIOTICS FOR USE AS ANTI-INFLAMMATORY AGENTS IN THE ORAL CAVITY

(71) Applicants: SYMRISE AG, Holzminden (DE); PROBI AB, Lund (SE)

(72) Inventors: Marcus Rudolf Götz, Oberweser (DE); Kerstin Holmgren, Helsingborg (SE); Niklas Larsson, Lund (SE); Bernd Fiebich, Freiburg (DE); William Wade, Clevedon (GB)

(73) Assignees: SYMRISE AG, Holzminden (DE); PROBI AB, Lund (SE)

( * ) Notice: Subject to any disclaimer, the term of this patent is extended or adjusted under 35 U.S.C. 154(b) by 0 days.

(21) Appl. No.: 16/070,553

(22) PCT Filed: Jan. 18, 2017

(86) PCT No.: PCT/EP2017/051005
§ 371 (c)(1),
(2) Date: Jul. 17, 2018

(87) PCT Pub. No.: WO2017/125447
PCT Pub. Date: Jul. 27, 2017

(65) Prior Publication Data
US 2019/0388485 A1    Dec. 26, 2019

(30) Foreign Application Priority Data
Jan. 19, 2016  (EP) ...................... 16151975

(51) Int. Cl.
| | | |
|---|---|---|
| *A61K 35/747* | (2015.01) | |
| *A61K 8/99* | (2017.01) | |
| *A61K 45/06* | (2006.01) | |
| *A61K 9/20* | (2006.01) | |
| *A61K 9/28* | (2006.01) | |
| *A61Q 11/00* | (2006.01) | |
| *A61K 9/68* | (2006.01) | |

(52) U.S. Cl.
CPC ............. *A61K 35/747* (2013.01); *A61K 8/99* (2013.01); *A61K 9/0058* (2013.01); *A61K 9/2095* (2013.01); *A61K 9/28* (2013.01); *A61Q 11/00* (2013.01); *A61K 45/06* (2013.01)

(58) Field of Classification Search
CPC ...... A61K 35/747; A61K 8/99; A61K 9/0058; A61K 9/2095; A61K 9/28; A61K 45/06
See application file for complete search history.

(56) References Cited

U.S. PATENT DOCUMENTS

| | | | | |
|---|---|---|---|---|
| 2008/0268006 A1* | 10/2008 | Molin | ................. | A61P 15/02 424/402 |
| 2009/0208469 A1* | 8/2009 | Alenfall | ................. | C12R 1/25 424/93.45 |
| 2010/0028449 A1 | 2/2010 | Prakash et al. | | |
| 2013/0209374 A1* | 8/2013 | Cune Castellana | ...... | A61K 8/99 424/48 |
| 2014/0023620 A1 | 1/2014 | Ioudina | | |
| 2014/0065218 A1* | 3/2014 | Lang | ................. | C12Q 1/04 424/474 |
| 2015/0238548 A1 | 8/2015 | Huang et al. | | |
| 2015/0240200 A1 | 8/2015 | Tsai et al. | | |
| 2015/0250834 A1 | 9/2015 | Tsai et al. | | |
| 2015/0328141 A1 | 11/2015 | Reindl et al. | | |
| 2017/0306289 A1 | 10/2017 | Chung et al. | | |

FOREIGN PATENT DOCUMENTS

| | | |
|---|---|---|
| CN | 101190239 A | 6/2008 |
| CN | 101703179 A | 5/2010 |
| CN | 101715908 A | 6/2010 |
| CN | 102470151 A | 5/2012 |
| CN | 104814983 A | 8/2015 |
| DE | 202009011379 U1 | 12/2010 |
| EP | 1634948 A1 | 3/2006 |
| EP | 1955702 A1 | 8/2008 |
| EP | 2364712 A1 | 9/2011 |
| EP | 2420580 A1 | 2/2012 |
| JP | 2014000039 A | 1/2014 |
| JP | 2014516957 A | 7/2014 |
| KR | 1020120035923 A | 4/2012 |
| RU | 2492851 C1 | 9/2013 |

(Continued)

OTHER PUBLICATIONS

U.S. Appl. No. 16/034,592; U.S. Appl. No. 16/070,573; U.S. Appl. No. 16/478,514 (Year: 2016).*
Snel et al. "Competitive Selection of Lactic Acid Bacteria That Persist in the Human Oral Cavity", Applied and Environmental Microbiology, Dec. 2011, p. 8445-8450 (Year: 2011).*
International Search Report and Written Opinion dated Mar. 16, 2018, for corresponding PCT Application No. PCT/EP2018/051112.

(Continued)

*Primary Examiner* — Ruth A Davis
(74) *Attorney, Agent, or Firm* — Polsinelli PC

(57) ABSTRACT

The present invention relates to certain microorganisms or mixtures thereof for use in the treatment and/or prevention of inflammation in the oral cavity, in particular for use in the treatment and/or prevention of dental caries and/or periodontal disease.

Figure 1A:
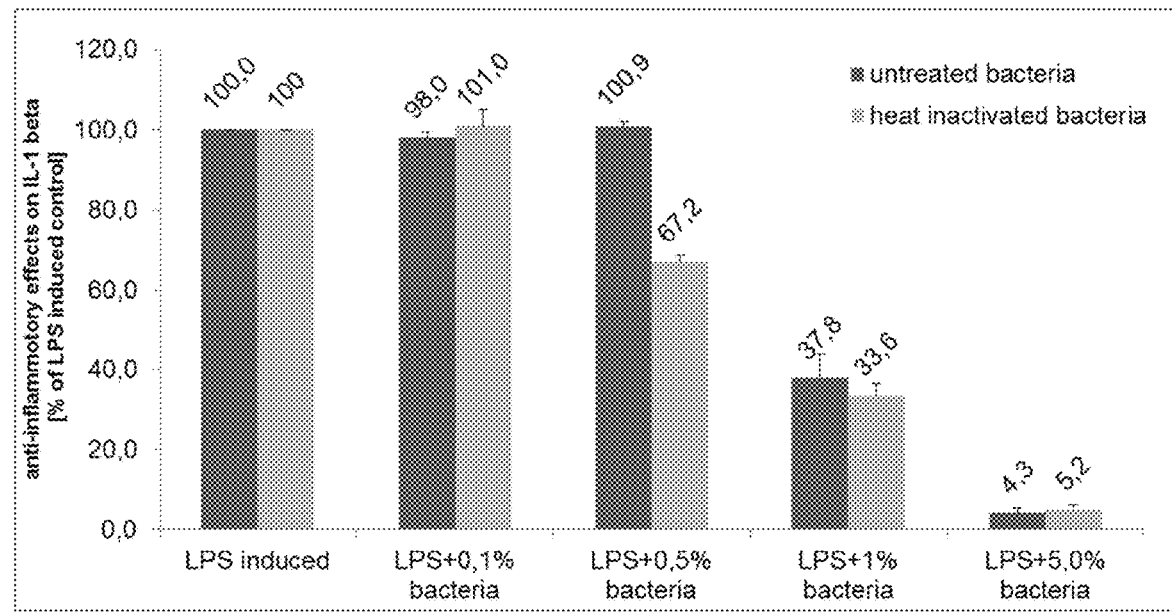
Figure 1B:
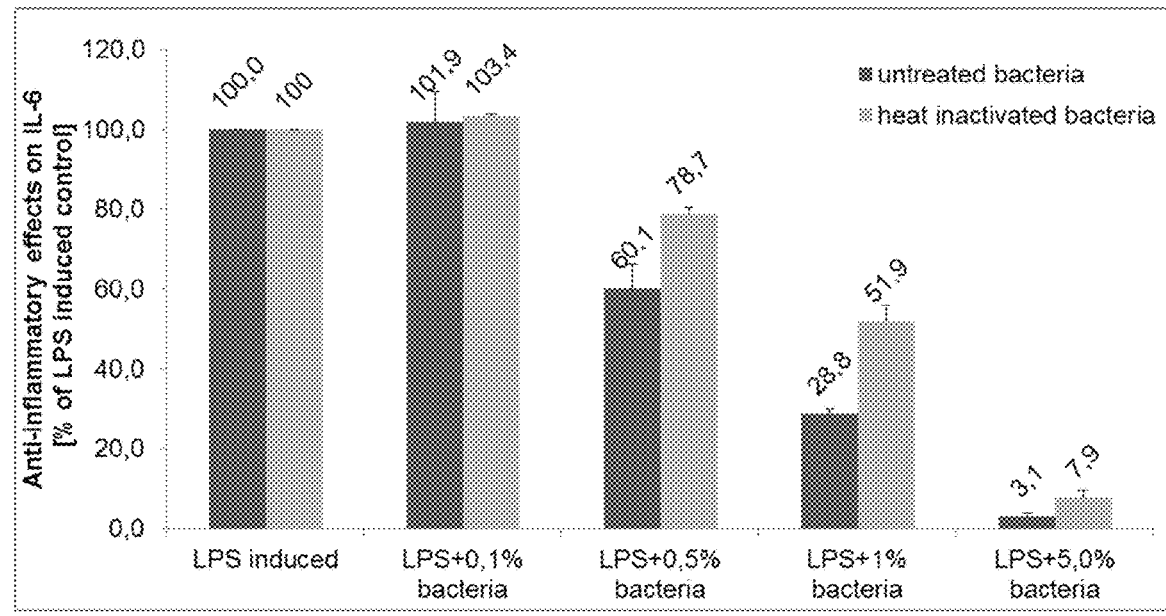
Figure 1C:
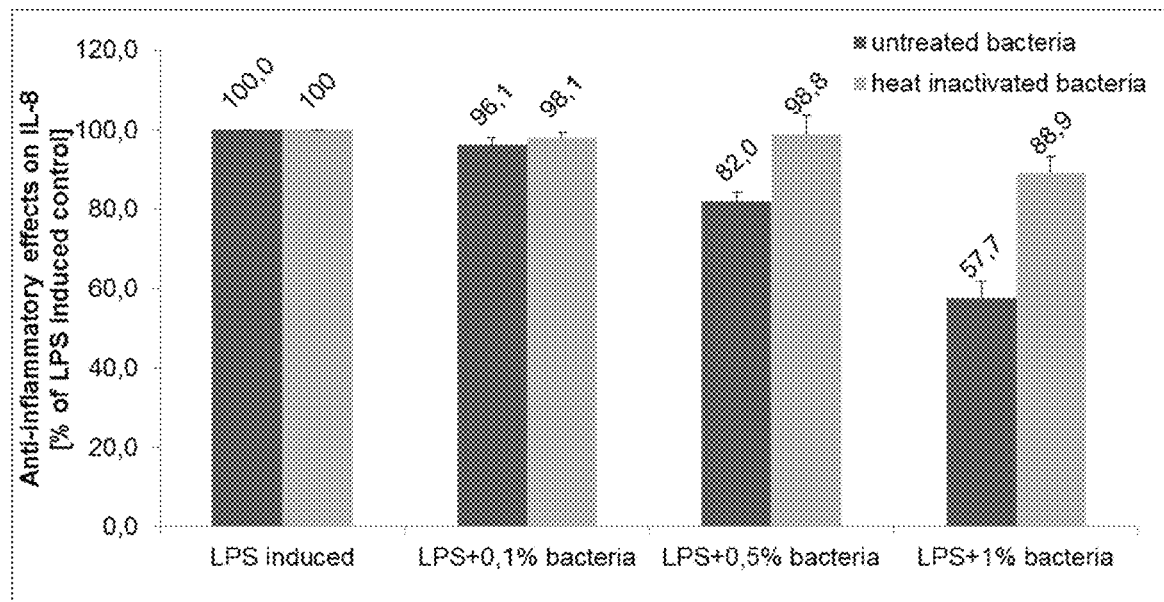
Figure 1D:
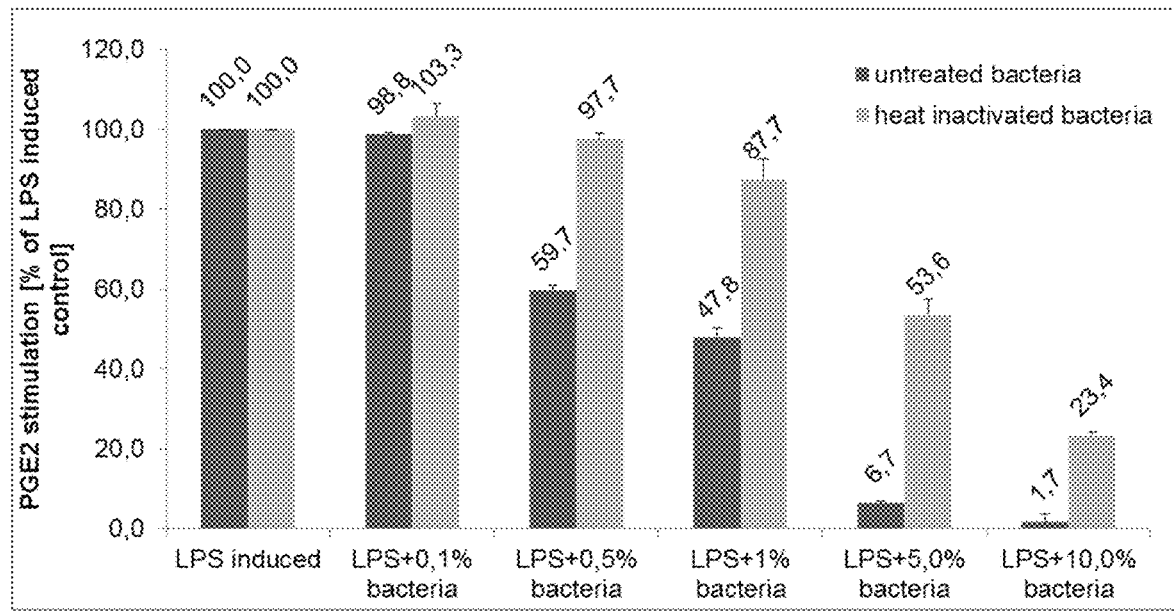
Figure 1E:
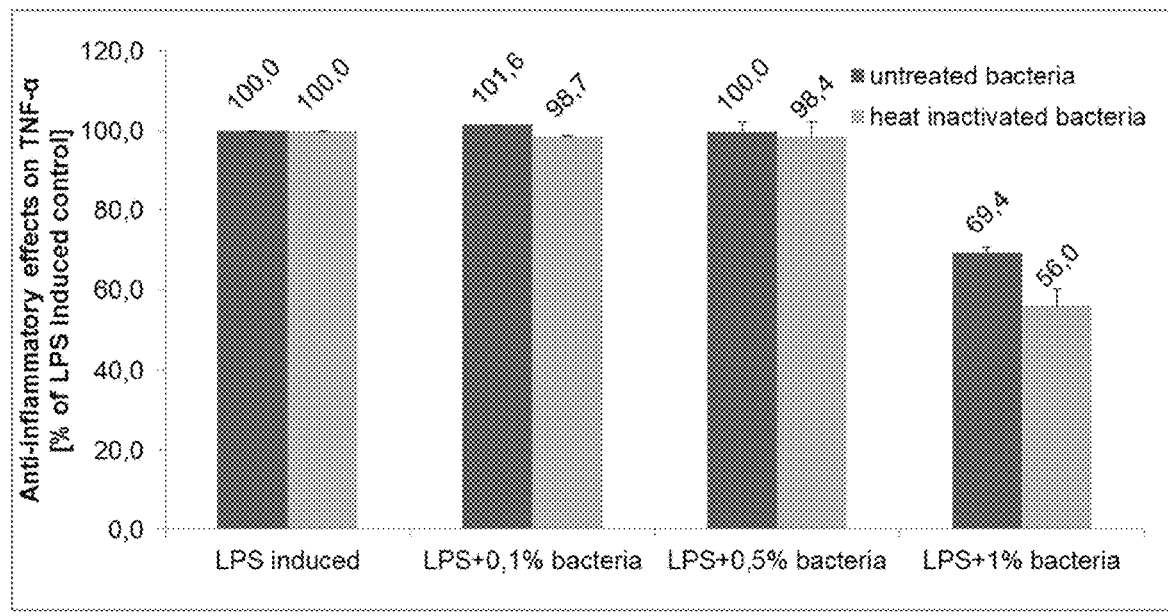
Figure 1F:
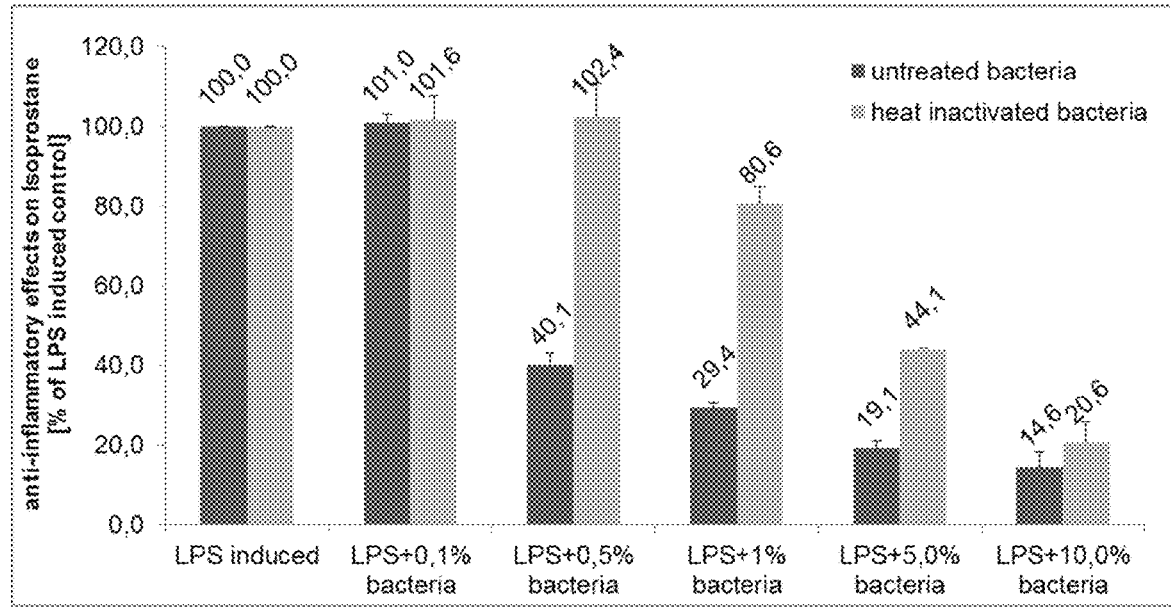

In particular, the present invention relates to microorganisms or mixtures thereof for use as an anti-inflammatory agent in the oral cavity for reducing or inhibiting the release of certain inflammatory factors.

Furthermore, the present invention provides oral pharmaceutical compositions, oral care products or products for nutrition or pleasure comprising one or more of the microorganisms as probiotic agents as well as a method of production thereof.

6 Claims, 18 Drawing Sheets

(56) References Cited

FOREIGN PATENT DOCUMENTS

| WO | 0078322 A2 | 12/2000 |
| WO | 2010077795 A2 | 7/2010 |
| WO | 2010099824 A1 | 9/2010 |
| WO | 2012022773 A1 | 2/2012 |
| WO | 2010064373 A1 | 5/2012 |
| WO | 2012156491 A1 | 11/2012 |
| WO | 2014140080 A1 | 9/2014 |
| WO | 2017035412 A1 | 3/2017 |
| WO | 2017125447 A1 | 7/2017 |

OTHER PUBLICATIONS

Snel, J. et al., "Competitive Selection of Lactic Acid Bacteria That Persists in the Human Oral Cavity", Applied and Environmental Microbiology, vol. 77, No. 23, 2011, pp. 8445-8450 XP055379435.
Roy, Byun et al., "Quantitative analysis of diverse *Lactobacillus* species present in advanced dental caries", Journal of Clinical Microbiology, American Society of Microbiology, vol. 42, No. 7, 2004, pp. 3128-3136 XP002488329.
Azcarate-Peril, M. A. et al., "Analysis of the Genome Sequence of Lactobacillus gasseri ATCC 33323 Reveals the Molecular Basis of an Autochthonous Intestinal Organism", Applied and Environmental Microbiology, vol. 74, No. 15, 2008, pp. 4610-4625 XP055029769.
International Preliminary Report on Patentability dated Jul. 24, 2018 for corresponding PCT Application No. PCT/EP2017/051011.
International Search Report and Written Opinion dated Mar. 10, 2017 for corresponding PCT Application No. PCT/EP2017/051011.
Anonymous: "Biogrowing—comprehensive probiotic solutions provider," 2015, XP002759385, pp. 1-16 www.biogrowing.com.
Sookkhee, S. et al., "Lactic acid bacteria from healthy oral cavity of Thai volunteers: Inhibition of oral pathogens," Journal of Applied Microbiology, vol. 90, No. 2, 2001, pp. 172-179.
Vuotto, Claudia et al., "Probiotics to counteract biofilm-associated infections: promising and conflicting data," International Journal of Oral Science, vol. 6, No. 4, 2014, pp. 189-194.
Chuang, Li-Chuan et al., "Probiotic effect on cariogenic bacterial flora," Clinical Oral Investigations, vol. 15, No. 4, 2010, pp. 471-476.
Korean Office Action dated Oct. 18, 2018 for corresponding Korean Patent Application No. 10-2018-7023803.
Chinese Office Action dated Jan. 11, 2019 for corresponding Chinese Patent Application No. 201780007278.3.
Chinese Office Action dated Apr. 3, 2019 for corresponding Chinese Application No. 201780007278.3.
Kistler, James O. et al.; "Development and pyrosequencing analysis of an in-vitro oral biofilm model," BMC Microbiology; 2015, pp. 1-10.
Japanese Office Action dated Dec. 10, 2018 for corresponding JP Application No. JP 2018-538205.
Australian Office Action dated Sep. 10, 2018 for corresponding AU Application No. 2017208481.
European Office Action dated Mar. 8, 2018 for corresponding EP Application No. EP 16151963.2.
Written Opinion dated Mar. 22, 2019 for corresponding PCT Application No. PCT/EP2018/067090.
Written Opinion dated Jul. 27, 2017 for corresponding PCT Application No. PCT/EP2017/051003.
Li, Allen, "Biogrowing probiotics brochure", 2015, p. 1, XP002758029.
International Search Report and Written Opinion dated Oct. 17, 2019 for corresponding PCT Application No. PCT/EP2019/067007.
Office Action dated Oct. 18, 2019 in co-pending U.S. Appl. No. 16/070,573
Biogrowing: "Dietary Supplements", 2010, pp. 1-3, XP002758028.
Iqbal, S. et al., "β-Galactosidase from *Lactobacillus plantarum* WCFS1: biochemical characterization and formation of prebiotic galacto-oligosaccharides," Carbohydrate Research, vol. 345, 2010, pp. 1408-1416.
International Search Report and Written Opinion dated Mar. 17, 2017 in corresponding PCT Application No. PCT/EP2017/051005.
Communication under Rule 71(3) EPC for European Patent Application No. 17700559.2 dated Feb. 4, 2020.
U.S. Final Office Action dated May 14, 2020 in co-pending U.S. Appl. No. 16/034,592.
https://en.wikipedia.org/wiki/Probiotic; 2020.
https://en.wikipedia.org/wiki/Lactobacillus_plantarum; 2020.
https://en.wikipedia.org/wiki/Lactobacillus; 2020.
https://en.wikipedia.org/wiki/Lactic_acid_bacteria; 2020.
Russian Search Report dated Mar. 26, 2020 for corresponding Russian Application No. 2018129759/04.
Roalnd J. Siezen et al., "Genomic diversity and versatility of *Lactobacillus plantarum*, a natural metabolic engineer," Microbial Cell Factories, vol. 10, 2011, pp. 1-13.
Stefan R. Herbel et al., "Timely approaches to identify probiotic species of the genus *Lactobacillus*," Gut Pathogens, vol. 5, No. 27, 2013, pp. 1-13.
Declaration by Dr. Niklas Larsson, 2020, pp. 1-15.
Juliana M. Ansari et al., "Strain-level diversity of commercial probiotic isolates of *Bacillus*, *Lactobacillus*, and *Saccharomyces* species illustrated by molecular identification and phenotypic profiling," Research article, 2019, pp. 1-19.
U.S. Appl. No. 16/478,514, filed Jul. 17, 2019.
U.S. Appl. No. 16/070,573, filed Jul. 17, 2018.
PCT/EP2018/067090, Jun. 26, 2018.
PCT/EP2017/051003, Jan. 18, 2017.
PCT/EP2019/067007, Jun. 26, 2019.
Japanese Office Action dated Jan. 14, 2021 for corresponding Japanese Application No. 2018-538221.

\* cited by examiner

PROBIOTICS FOR USE AS ANTI-INFLAMMATORY AGENTS IN THE ORAL CAVITY

CROSS-REFERENCE TO RELATED APPLICATIONS

This application is a national stage application (under 35 U.S.C. § 371) of PCT/EP2017/051005, filed Jan. 18, 2017, which claims benefit of European Application No. 16151975.6, filed Jan. 19, 2016, which are incorporated herein by reference in their entireties.

The present invention relates to certain microorganisms or mixtures thereof for use in the treatment and/or prevention of inflammation in the oral cavity, preferably for the treatment and/or prevention of gingivitis and/or peridontitis.

In particular, the present invention relates to microorganisms or mixtures thereof for use as anti-inflammatory agents in the oral cavity for reducing or inhibiting the release of one or more inflammatory factors selected from the group consisting of interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and NF-$_\kappa$B.

Furthermore, the present invention provides oral pharmaceutical compositions, oral care products or products for nutrition or pleasure comprising one or more of the anti-inflammatory microorganisms as active agents as well as a method of production thereof.

Inflammatory conditions of the gums are primarily induced by the formation of dental plaque. Colonizing bacteria form a biofilm on the surface of the teeth aided by the presence of food residues as well as components of saliva. If not sufficiently cleared away at an early stage, plaque films on the surface of the teeth result in deposition of dental calculus which is very hard to remove. The presence of raised numbers of bacteria at the gingival margin leads to inflammation of the gingivae, known as gingivitis. In susceptible individuals, gingivitis may progress to peridontitis, which can lead to tooth loss. In particular, lipopolysaccharides (LPS) present in Gram-negativ bacteria can cause a non-specific immune response by LPS-stimulated macrophages, which release prostaglandin E2 (PEG2) and pro-inflammatory mediators such as interleukins and TNF-$\alpha$ in the affected tissue. The pro-inflammatory mediators induce the release of further PGE2s and matrix metalloproteinases (MMPs) from the residing fibroblasts, which destroy the extracellular matrix of the surrounding tissue. This allows bacteria to penetrate deeper into the tissue and promote the inflammatory process independent of the outer layer of the epithelium and the dental root causing the formation of a periodontal pocket. The alveolar bone supporting the tooth resorbs ahead of the advancing bacteria, causing the tooth to become unstable and, if left untreated, lost.

In order to avoid progressive destruction of the gums, inflammatory responses in the oral cavity need to be suppressed in the early stages or ideally prevented.

Many different approaches have addressed this problem, ranging from improved methods for the mechanical removal of plaque to the use of oral care products with strong anti-bacterial properties.

However, not all the bacteria present in the oral cavity are disease-associated and many even promote oral health. Therefore, it is desirable to establish a balance towards a healthy composition of the mouth microbiota instead of non-specifically eradicating resident bacteria.

The normal oral microbiota is highly complex and includes over 700 bacterial species as well as archaea, fungi, protozoa and viruses. Lower gut commensals such as lactobacilli and bifidobacteria have been shown to have beneficial effects on gut health, including some anti-inflammatory properties, when administered as probiotics.

Probiotic action of bacteria in the oral cavity has been subject to some research but it has been found to vary strongly with the species used and suitable parameters for efficient application are hard to establish because the action may rely on largely unrelated effects.

Among the probiotic actions, general anti-bacterial effects against disease-associated species, the reduction or prevention of bacterial adhesion to the surface of the teeth as well as anti-inflammatory effects have been discussed in the literature.

WO 2010/077795 A2 relates to compositions to improve oral health comprising a therapeutically effective amount of beneficial bacteria selected from specific strains of streptococci and lactobacilli. While WO 2010/077795 A2 is mainly concerned with reducing the incidence of aspiration pneumonia, the prevention of gingivitis and plaque by balancing the mouth flora towards beneficial bacteria is also mentioned and it is stated generally, that probiotics may compete with receptor signaling sites that mediate systemic inflammation. However, these properties are not further discussed in particular with respect to different inflammatory factors and such effects were not evaluated for the disclosed bacterial strains.

Probiotics containing teeth and oral care products are disclosed as being capable of preventing parodontitis and gingivitis according to DE 20 2009 011 370 U1, which recites a large variety of probiotic bacteria including lactobacilli, bifidobacteria, enterococci, sporolactobacilli and streptococci. Specific strains are not mentioned, however, and the alleged probiotic action is not further evaluated.

A method for administering probiotics such as lactobacilli, bifidobacteria or streptococci to reduce/prevent inflammatory conditions is presented in US 2008/0241226 A1.

WO 2010/008879 A2 provides a confectionary composition containing an inactive probiotic, which is activable upon contact with water. As probiotics, different strains of lactobacilli and bifidobacteria are disclosed. Probiotic effects mentioned in WO 2010/008879 A2 include the reduction of gum inflammation for example by suppressing pathogenic bacteria.

The improvement of oral and dental health by the probiotic strain *Lactobacillus rhamnosus* GG, ATCC 53103 is described in US 20040101495. In this context, a stimulating effect of probiotics on the immune system is disclosed.

The ability of probiotic bacteria to alter the balance of pro-inflammatory and anti-inflammatory cytokines is mentioned in WO 2012/022773 A1, where *Lactobacillus reuteri* ATCC 55730 is cited as being capable to reduce gingivitits by influencing the levels of inflammatory mediators in gingival crevicular fluid. WO 2012/022773 A1, however, is primarily concerned with probiotic compositions for oral health comprising effective amounts of *Lactobacillus plantarum* CECT 7481 and *Lactobacillus brevis* CECT 7480, which are demonstrated to have anti-bacterial properties against certain pathogens.

In summary, little is known about the influence of specific probiotic strains on inflammatory reactions in the oral cavity, in particular with respect to the suppression of different inflammatory mediators. Remarkably, it has been found out in the extensive investigations leading up to the present invention, that some strains of generally acknowledged probiotic bacteria may also enhance the release of pro-inflammatory factors at certain doses. Therefore, the composition of probiotic oral care products still requires detailed studies on the pro- and anti-inflammatory effects of the (commercially) available strains in order to optimize the beneficial effects for application.

An objective of the present invention was to provide microorganisms or mixtures thereof which can be used in highly effective treatment and/or prevention of inflammation in the oral cavity, in particular in the treatment and/or prevention of gingivitis and/or peridontitis.

A further objective of the present invention was to provide microorganisms or mixtures thereof which are capable to reduce or inhibit the release of one or more inflammatory factors such as interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and $NF-_{\kappa}B$.

Oral care compositions or products for delivering the microorganism according to the invention and a method for producing such compositions or products are also provided.

The objective of the present invention is met by a microorganism or mixture comprising or consisting of two or more microorganisms for use in the treatment and/or prevention of inflammation in the oral cavity, preferably for use in the treatment and/or prevention of gingivitis and/or peridontitis,
wherein the microorganism(s) is/are selected from the group consisting of *Lactobacillus paracasei* LPc-G110 (CCTCC M 2013691), *Lactobacillus plantarum* GOS 42 (DSM 32131), *Lactobacillus delbrueckii* subsp. *lactis* LL-G41 (CCTCC M 2016652), *Lactobacillus plantarum* Heal19 (DSM 15313) and *Lactobacillus paracasei* NS9 (NCIMB 8823).

By extensive screenings, the bacterial strains according to the invention have been identified to exhibit distinct modulating activity mostly in an inhibitive manner against the release of certain pro-inflammatory factors while, at the same time, they do not or only negligibly enhance the release of other pro-inflammatory factors. The prior art has not evaluated the efficacy of different bacterial strains with respect to the inhibition of certain pro-inflammatory factors and enhancement of others and only generally refers to beneficial effects on the balance of pro-inflammatory and anti-inflammatory cytokines. The present invention now allows for an optimized use of commercially available probiotic bacterial strains for the prevention and/or treatment of inflammatory conditions in the oral cavity which has not been possible before.

The strain *Lactobacillus paracasei* LPc-G110 has been deposited under the Budapest Treaty at the China Center for Type Culture Collection (CCTCC), Wuhan University, Wuhan 430072, China, under the accession number CCTCC M 2013691 by BioGrowing Co., Ltd., No. 10666 Songze Rd., Qingpu Shanghai 201700, China, on 23 Dec. 2013, and the strain *Lactobacillus plantarum* GOS 42 has been deposited under the Budapest Treaty at the Leibniz Institut Deutsche Sammlung für Mirkoorganismen und Zellkulturen GmbH (DSMZ), Inhoffenstr. 7B, 38124 Braunschweig, Germany, by Probi AB under the accession number DSM 32131 on 2 Sep. 2015. The strain *Lactobacillus delbrueckii* subsp. *lactis* LL-G41 has been deposited under the Budapest Treaty at the China Center for Type Culture Collection (CCTCC), Wuhan University, Wuhan 430072, China under the accession number CCTCC M 2016652 by BioGrowing Co., Ltd., No. 10666 Songze Rd., Qingpu Shanghai 201700, China, on 17 Nov. 2016, and the strain *Lactobacillus plantarum* Heal19 has been deposited under the Budapest Treaty at the Leibniz Institut Deutsche Sammlung für Mirkoorganismen und Zellkulturen GmbH (DSMZ) Inhoffenstr. 7B, 38124 Braunschweig, Germany, under the accession number DSM 15313 by Probi AB on 27 Nov. 2002. The strain *Lactobacillus paracasei* NS9 is publicly available at the National Collection of Industrial, Food and Marine Bacteria, UK, (NCIMB), Ferguson Building, Craibstone Estate, Bucksburn, Aberdeen AB21 9YA, United Kingdom, under the accession number NCIMB 8823 (date of accession 1 Oct. 1956, deposited by University of Birmingham).

Preferable anti-inflammatory probiotics and probiotic materials show their efficacy in a sequential testing in which their anti-inflammatory effects in human primary monocytes are determined and—if promising—verified by assessing the anti-inflammatory effects in fibroblasts. Namely, as inflammatory parameters, interleukin 1-beta (IL-1-beta), interleukin 6 (IL-6), interleukin 8 (IL-8), tumor necrosis factor alpha (TNFalpha), prostaglandin E2 (PGE2), 8-isoprostane and matrix metallopeptidase 9 (MMP9) have been evaluated in human primary monocytes while PGE2, IL-6, IL-8, 8-isoprostane and $NF-_{\kappa}B$ activation were determined in human gingival fibroblasts.

*Lactobacillus plantarum* Heal19 was selected as a potent agent for modulation of anti-inflammatory responses. In the validated primary human monocyte model it significantly down regulated the expression of selected biomarkers. Key regulators dampened by this strain are: IL1-beta and PGE-2, which are stimulators of early inflammation manifesting in increased secretion of acute phase proteins, IL-6, a transition-switch from innate to acquired immunity or IL-8, an inducer of the chemotactical recruitment of neutrophils as well as Isoprostane, a mediator of pain. Moreover, *Lactobacillus plantarum* Heal19 shows similar albeit less pronounced effects once attenuated on inflammatory markers IL-1 and PGE2.

*Lactobacillus paracasei* NS9 serves as a potent modulator of inflammatory responses in a viable as well as in an attenuated state. In the validated primary human monocyte model it significantly down regulated the expression of selected biomarkers. Key regulators dampened by this strain are: IL1-beta and PGE-2, which are stimulators of early inflammation manifesting in increased secretion of acute phase proteins, IL-6, a transition-switch from innate to acquired immunity or TNF-alpha, a general marker for local and systematic inflammation as well as Isoprostane, a mediator for pain. Most interestingly, even in an attenuated state as paraprobiotic all above mentioned markers are down regulated albeit to a lesser extent. Nevertheless, *Lactobacillus paracasei* NS9 is the most potent modulator of the inflammatory response also in an attenuated state.

*Lactobacillus delbrueckii* subsp. *lactis* LL-G41 is one of the strongest modulators of inflammatory responses in a viable state. In the validated primary human monocyte model it significantly down regulated the expression of selected biomarkers. Key regulators dampened by this strain are: IL1-beta and PGE-2, which are stimulators of early inflammation manifesting in increased secretion of acute phase proteins, IL-6, a transition-switch from innate to acquired immunity or TNF-alpha, a general marker for local and systematic inflammation, IL-8, an inducer of the chemotactical recruitment of neutrophils as well as Isoprostane, a mediator for pain. Most interestingly, even in an attenuated state as paraprobiotic PGE-2, IL-6 and IL-8 are down regulated albeit to a lesser extent.

As explained above, the colonization of the oral mucosa by disease-associated bacteria and the formation of plaque can tip the microbial balance in the oral cavity towards an accumulation of detrimental microorganisms, which is also referred to as dysbiosis. Therefore, the microorganisms for use in the prevention and/or treatment of inflammation in the oral cavity according to the invention includes the use in the prevention and/or treatment of plaque and plaques associated diseases and advantageously aides to avoid oral dysbiosis by balancing the mouth flora towards a healthy state.

In a preferred embodiment of the present invention the microorganism(s) described above is/are (an) attenuated or (a) dead microorganism(s), preferably (a) heat-inactivated microorganism(s), preferably (a) microorganism(s) heat-inactivated by incubation for 2 to 8 minutes at a temperature between 70 and 100° C.

In the studies described below, it has been demonstrated that the microorganism according to the invention are capable to provide inhibitory effects on the release of pro-inflammatory factors even in an inactivated state. Therefore it is also possible to use dead or for example heat-inactivated microorganisms. Remarkably, heat inactive strains may show the same or even slightly enhanced anti-inflammatory activity towards certain factors.

In one aspect, the present invention relates to the microorganism(s) recited above for use as anti-inflammatory agents in the oral cavity for reducing or inhibiting the release of one or more inflammatory factors selected from the group consisting of interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and NF-$_\kappa$B.

For the first time it has now been elucidated individually which probiotic strains are capable of efficiently inhibiting the release of a number of different pro-inflammatory factors. It is therefore possible to optimize the use of probiotic strains for the treatment and/or prevention of inflammatory conditions in the oral cavity by selecting the overall most efficient strain(s).

According to another aspect of the present invention, fragments of one or more microorganism(s) as defined in any of the aspects described above may be used in the treatment and/or prevention of inflammation in the oral cavity, preferably in the treatment and/or prevention of gingivitis and/or peridontitis.

It may not be necessary to use whole cells of the probiotic microorganisms according to the invention as mixtures comprising only fragments (e.g. debris of degraded cells) of the microorganisms are sufficient to provide the inventive effects.

In a further aspect, the present invention also relates to an oral pharmaceutical composition, oral care product or product for nutrition or pleasure, comprising one or more microorganism(s) selected from the group consisting of *Lactobacillus paracasei* LPc-G110 (CCTCC M 2013691), *Lactobacillus plantarum* GOS 42 (DSM 32131), *Lactobacillus delbrueckii* subsp. *lactis* LL-G41 (CCTCC M 2016652), *Lactobacillus plantarum* Heal19 (DSM 15313) and *Lactobacillus paracasei* NS9 (NCIMB 8823) or fragments thereof, wherein the total amount of the microorganism(s) or the fragments thereof is sufficient for treating and/or preventing inflammation in the oral cavity, preferably for treating and/or preventing gingivitis and/or peridontitis, further preferably wherein the total amount of the microorganism(s) or the fragments thereof is in the range from 0.01 to 100%, more preferably in the range from 0.1 to 50%, most preferably in the range from 1 to 10%, in each case with respect to the total weight of the composition, and/or wherein the total amount of the microorganism(s) or the fragments thereof is in the range from $1\times10^3$ to $1\times10^{11}$ colony forming units (CFU), more preferably in the range from $1\times10^5$ to $1\times10^{10}$ CFU.

The skilled person is aware that the probiotic organisms used in a composition or product according to the invention represent biologic material the activity of which may vary with the batch and depends also on the production or processing method. Therefore, the suitable amount can be adjusted accordingly within the given range.

Furthermore, the present invention relates to a composition or product as described above for use in the treatment and/or prevention of inflammation in the oral cavity, preferably for use in the treatment and/or prevention of gingivitis and/or peridontitis.

A composition according to the invention may further comprise one or more components selected from the group consisting of carriers, excipients or further active ingredients such as, for example, active agents from the group of non-steroidal antiphlogistics, antibiotics, steroids, anti-TNF-alpha antibodies or other biotechnologically produced active agents and/or substances as well as analgetics, dexpanthenol, prednisolon, polyvidon iodide, chlorhexidine-bis-D-gluconate, hexetidine, benzydamine HCl, lidocaine, benzocaine, macrogol lauryl ether, benzocaine in combination with cetidyl pyridinium chloride or macrogol lauryl ether in combination with protein free hemodialysate from calf blood, as well as for example fillers (e.g. cellulose, calcium carbonate), plasticizer or flow improves (e.g. talcum, magnesium stearate), coatings (e.g. polyvinyl acetate phtalate, hydroxyl propyl methyl cellulose phtalate), disintegrants (e.g. starch, cross-linking polyvinyl pyrrolidone), softener (e.g. triethyl citrate, dibutyl phthalate) substances for granulation (lactose, gelatin), retardation (e.g. poly (meth)acrylic acid methyl/ethyl/2-trimethyl aminomethyl ester copolymerizates in dispersion, vinyl acetate/crotonic acid copolymerizates), compaction (e.g. microcrystalline cellulose, lactose), solvents, suspending or dispersing agents (e.g. water, ethanol), emulsifiers (e.g. cetyl alcohol, lecithin), substances for modifying the rheological properties (silica, sodium alginate), substances for microbial stabilization (e.g. benzalkonium chloride, potassium sorbate), preservatives and antioxidants (e.g. DL-alpha-tocopherol, ascorbic acid) substances for modifying pH (lactic acid, citric acid), blowing agents or inert gases (e.g. fluorinated chlorinated hydrocarbons, carbon dioxide), dyes (iron oxide, titanium oxide), basic ingredients for ointment (e.g. paraffines, bees wax) and others as described in the literature (e.g. in Schmidt, Christin. Wirk- und Hilfsstoffe für Rezeptur, Defektur und Großherstellung. 1999; Wissenschaftliche Verlagsgesellschaft mbH Stuttgart oder Bauer, Frömming Führer. Lehrbuch der Pharmazeutischen Technologie. 8. Auflage, 2006. Wissenschaftliche Verlagsgesellschaft mbH Stuttgart).

A composition or product according to the present invention may also be coated or encapsulated.

Encapsulation of a composition according to the invention may have the advantage of allowing a controlled release, for example upon contact with water, or a continuous release over an extended period of time. Moreover, the composition may be protected from degradation improving the shelf life of the product. Methods for encapsulation of active ingredients are well known in the art and a number of encapsulation materials as well as methods how to apply them to a composition according to specific requirements are available.

Furthermore, a composition or product according to the invention may be in the form of a solution, suspension, emulsion, tablets, granules, powder or capsules.

The composition or product according to the invention may be selected form the group consisting of toothpaste, tooth gel, tooth powder, tooth cleaning liquid, tooth cleaning foam, mouth wash, mouth spray, dental floss, chewing gum and lozenges.

Such compositions or products may contain abrasive systems (abrasive and/or polishing components) such as silicates, calcium carbonate, calcium phosphate, aluminum oxide and/or hydroxyl apatite, surfactants such as e.g. sodium lauryl sulfate, sodium lauryl sarcosinate and/or cocamidopropyl betaine, humectants such as glycerol and/or sorbitol, thickening agents, e.g. carboxy methyl cellulose, poly ethylene glycols, carrageenans and/or Laponite®, sweeteners such as saccharine, aroma and taste correcting agents for unpleasant taste impressions, taste modifying substances (e.g. inositol phosphate, nucleotides, e.g. guanosine monophosphate, adenosine monophosphate or other substances, e.g. sodium glutamate or 2-phenoxy propionic acid), cooling agents such as menthol derivatives (e.g. L-mentyl lactate, L-menthyl alkyl carbonate, menthone ketals), icilin and icilin derivates, stabilizers and active agents such as sodium fluoride, sodium monofluoro phosphate, tin difluoride, quarternary ammonium fluorides, zinc citrate, zinc sulfate, tin pyrophosphate, tin dichloride, mixtures of different pyrophosphates, triclosane, cetyl pyridinium chloride, aluminum lactate, potassium citrate, potassium nitrate, potassium chloride, strontium chloride, hydrogen peroxide, aroma substances, sodium bicarbonate and/or smell correcting agents.

Chewing gums or dental care chewing gums may comprise a chewing gum base comprising elastomers, e.g. polyvinyl acetate (PVA), polyethylene, (low or medium molecular) polyiso butane (PIB), polybutadiene, isobutene/isoprene copolymers, polyvinyl ethyl ether (PVE), polyvinyl butyl ether, copolymers of vinyl esters and vinyl ethers, styrene/butadiene copolymers (SBR) or vinyl elastomers, e.g. based on vinyl acetate/vinyl laurate, vinyl acetate/vinyl stearate or ethylene/vinyl acetate and mixtures of the mentioned elastomers as e.g. example described EP 0 242 325, U.S. Pat. Nos. 4,518,615, 5,093,136, 5,266,336 5,601,858 or 6,986,709. Additionally chewing gum bases may contain further ingredients, e.g. (mineral) filers, e.g. calcium carbonate, titanium dioxide, silicone dioxide, talcum, aluminum oxide, dicalcium phosphate, tricalcium phosphate, magnesium hydroxide and mixtures thereof, plasticisers (e.g. lanolin, stearic acid, sodium stearate, ethyl acetate, diacetin (glycerol diacetate), triacetin (glycerol triacetate) and trietyhl citrate), emulsifiers (e.g. phosphatides, such as lecithin and mono and diglycerides of fatty acids, e.g. glycerol monostearate), antioxidants, waxes (e.g. paraffine waxes, candelilla waxes, carnauba waxes, microcrystalline waxes and polyethylene waxes), fats or fatty oils (e.g. hardened (hydrogenated) plant or animal fats) and mono, di or triglycerides.

Finally, the present invention also relates to a method of producing an oral pharmaceutical composition, an oral care product or a product for nutrition or pleasure as described above, comprising the following step:

combining one or more microorganism(s), selected from the group consisting of *Lactobacillus paracasei* LPc-G110 (CCTCC M 2013691), *Lactobacillus plantarum* GOS 42 (DSM 32131), *Lactobacillus delbrueckii* subsp. *lactis* LL-G41(CCTCC M 2016652), *Lactobacillus plantarum* Heal19 (DSM 15313) and *Lactobacillus paracasei* NS9 (NCIMB 8823) or fragments thereof to one or more further components, preferably to one or more components selected form the group consisting of carriers, excipients or further active ingredients.

In the context of the present invention, also described herein is a method of treating a subject or, respectively, patient, in particular for treating and/or preventing of inflammation in the oral cavity (as described herein), comprising administering the herein described microorganisms or mixtures to a subject/patient, preferably to a subject/patient in need thereof, preferably in an amount sufficient to treat or prevent inflammation.

SHORT DESCRIPTION OF THE FIGURES

FIG. 1 shows the anti-Inflammatory effects of *Lactobacillus paracasei* LPc-G110 (CCTCC M 2013691) in human primary monocytes on interleukin 1 beta (A), interleukin 6 (B), interleukin 8 (C), prostaglandin E2 (D), tumor necrosis factor alpha (E) and isoprostane (F). The left column refers to untreated cells, the right column to attenuated cells.

Figure 2A:
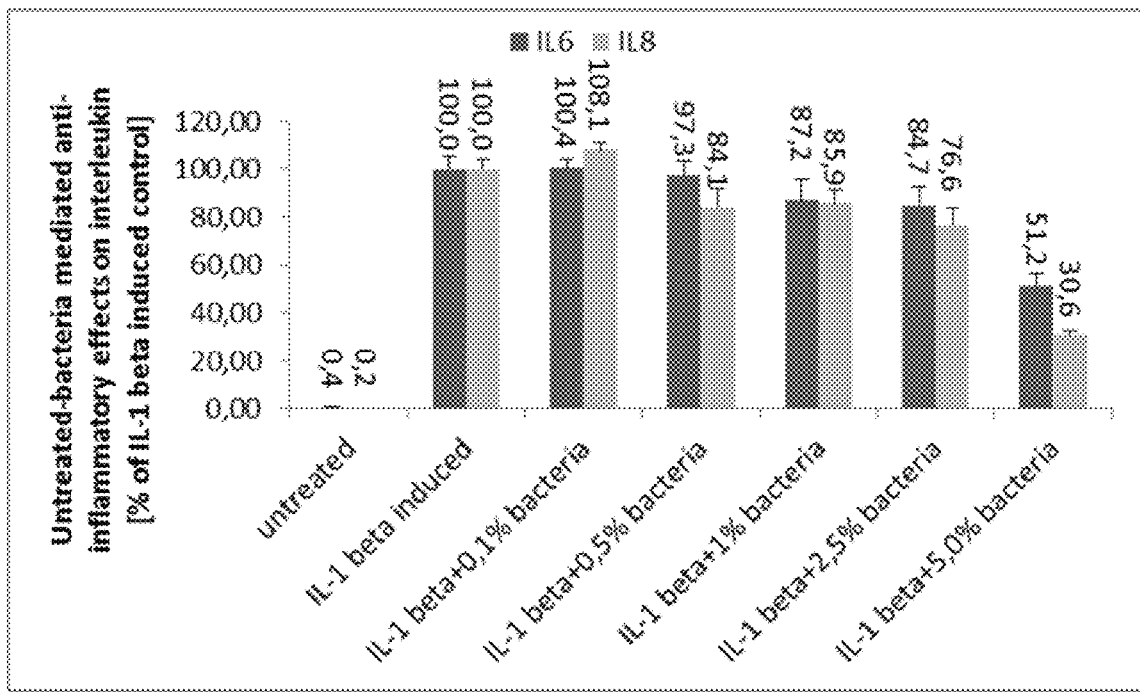
Figure 2B:
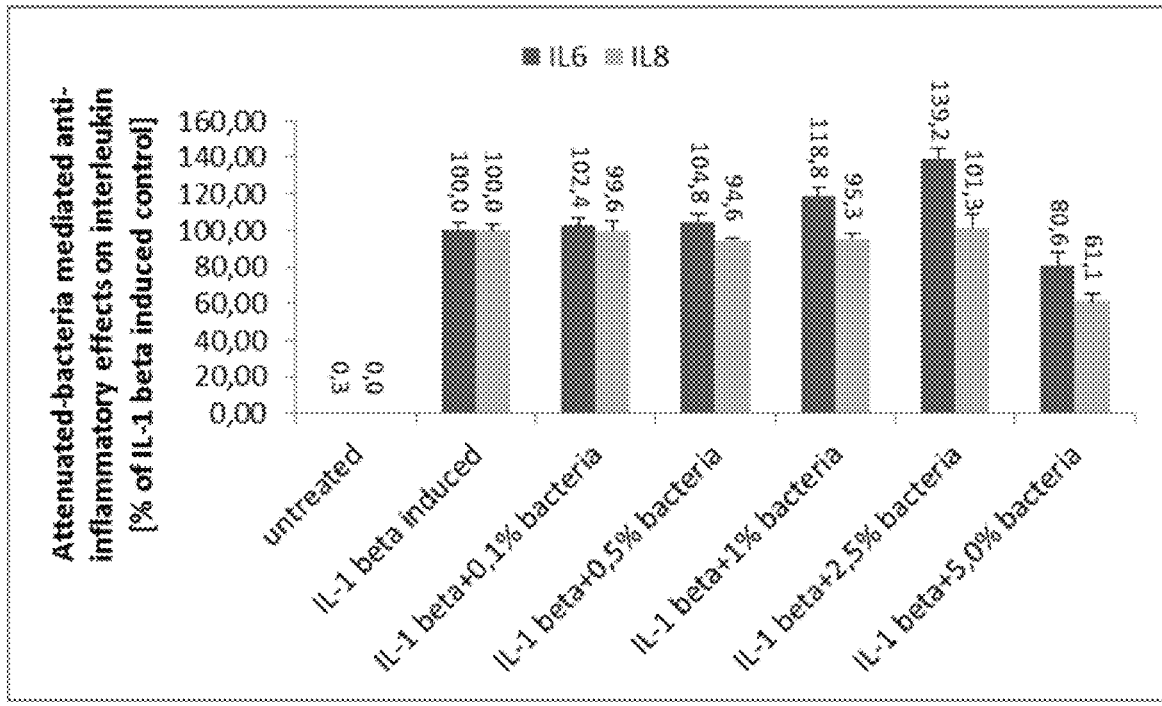
Figure 3A:
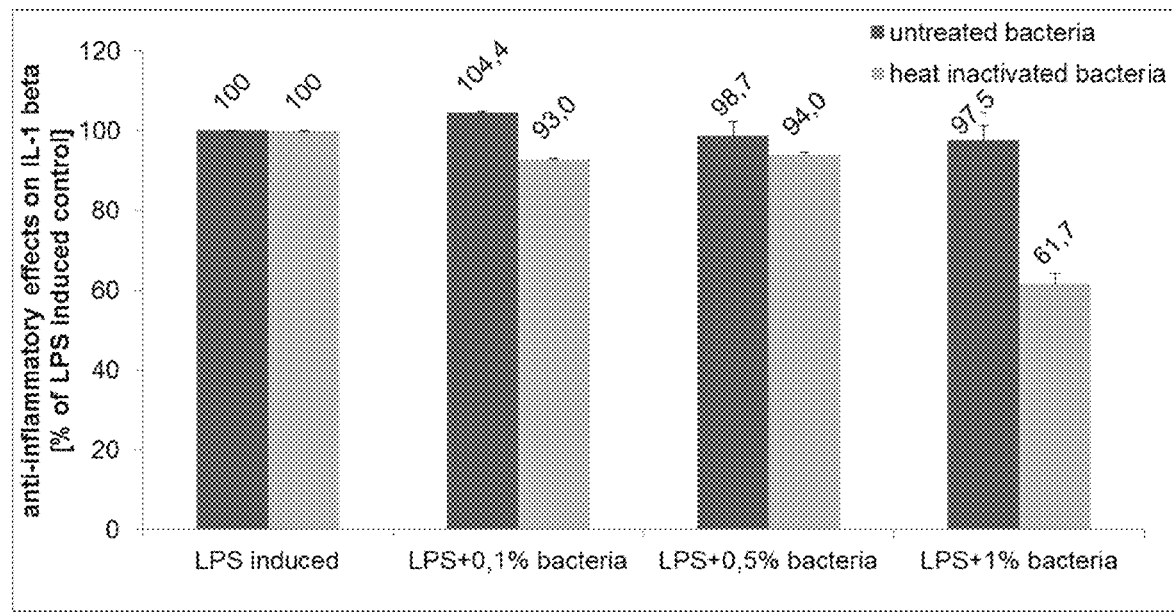
Figure 3B:
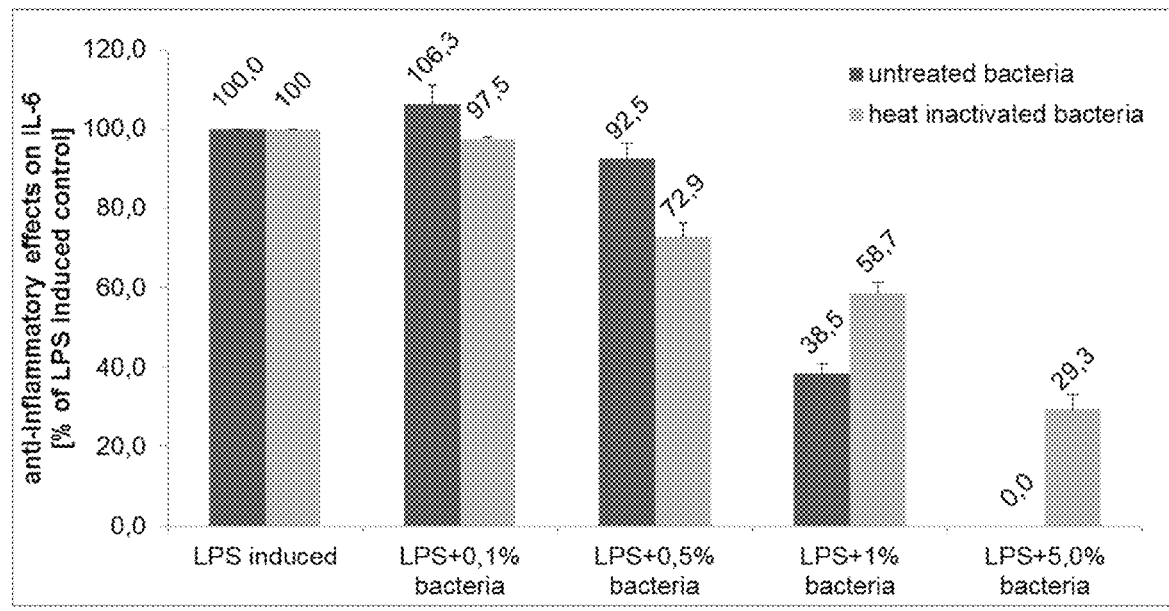
Figure 3C:
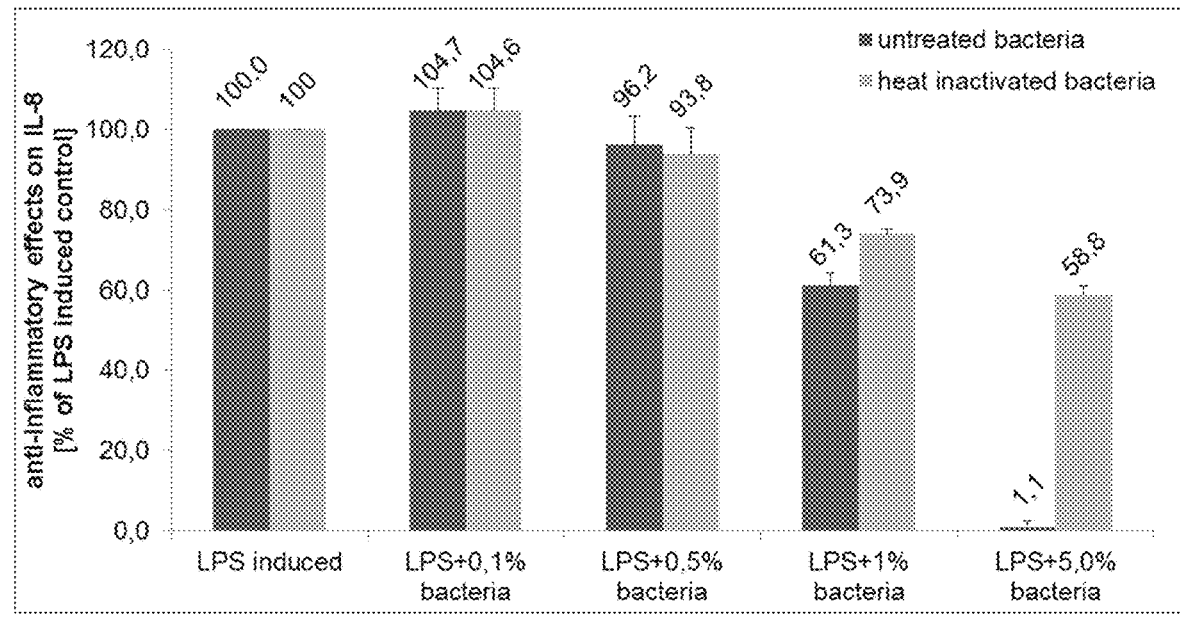
Figure 3D:
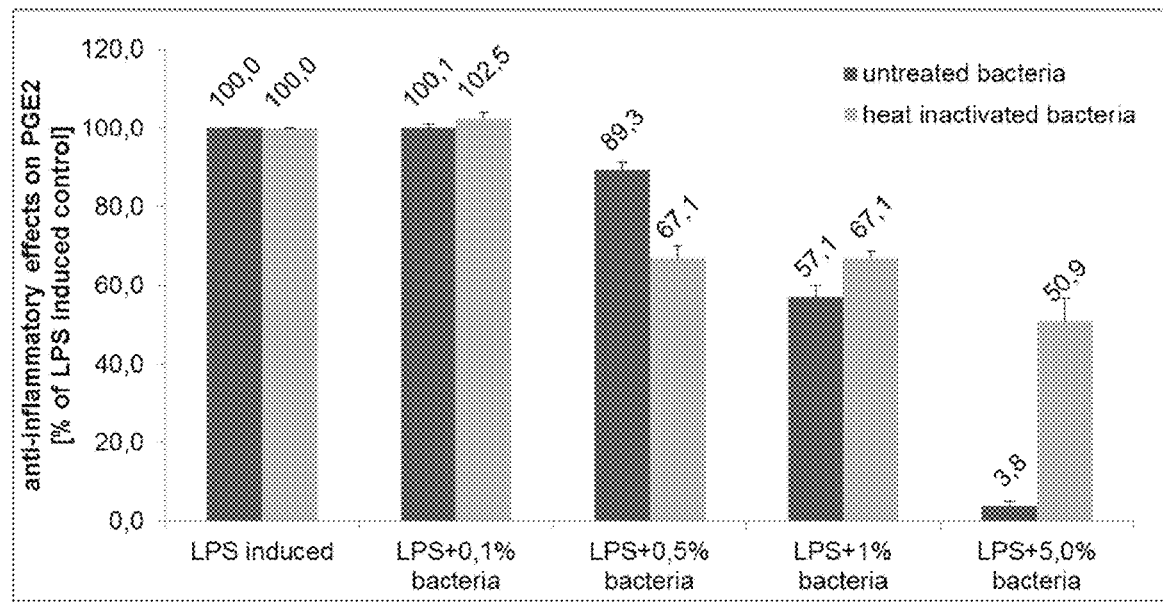
Figure 3E:
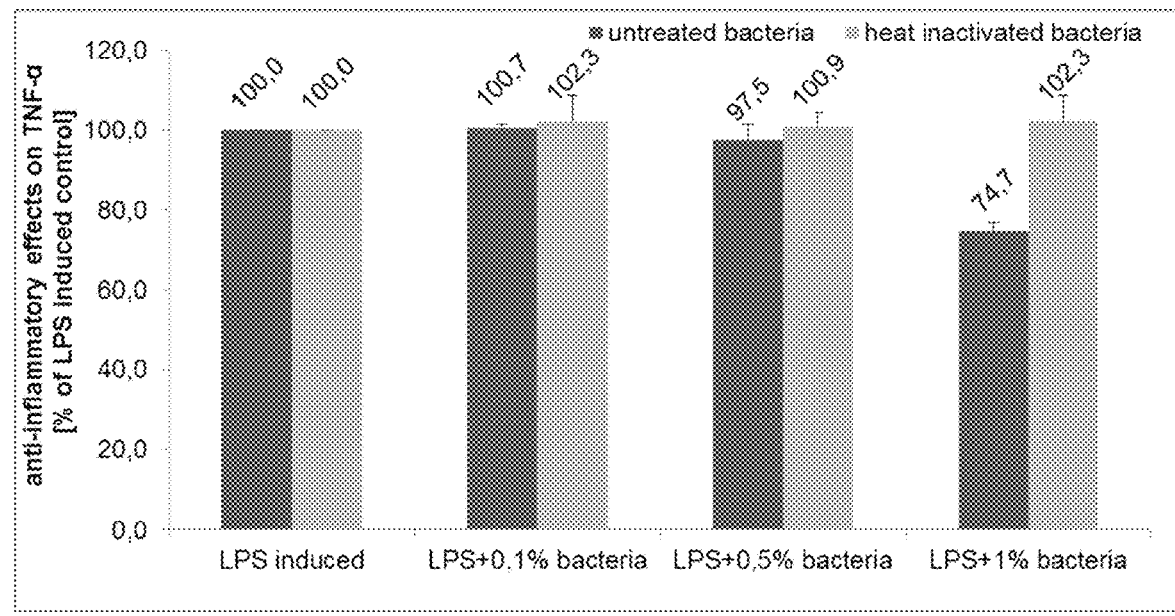
Figure 3F:
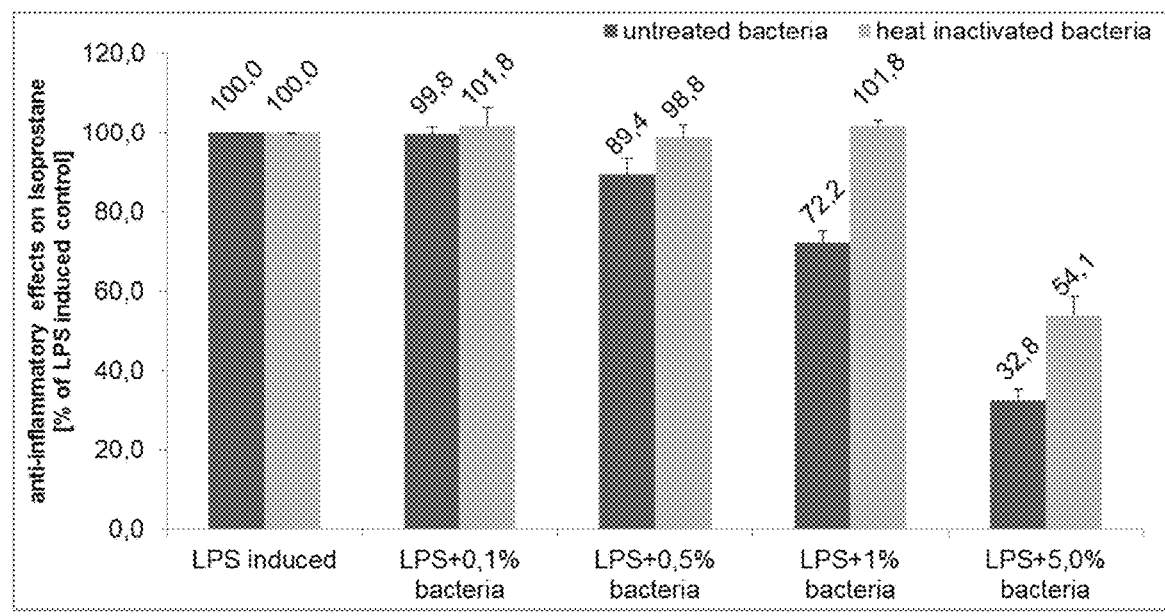

FIG. 2 shows the anti-Inflammatory effects of *Lactobacillus paracasei* LPc-G110 (CCTCC M 2013691) in untreated (A) and attenuated (B) form on interleukin in human gingival fibroblasts. The left column refers to interleukin 6, the right column to interleukin 8.

FIG. 3 shows the anti-Inflammatory effects of *Lactobacillus plantarum* GOS 42 (DSM 32131) in human primary monocytes on interleukin 1 beta (A), interleukin 6 (B), interleukin 8 (C), prostaglandin E2 (D), tumor necrosis factor alpha (E) and isoprostane (F). The left column refers to untreated cells, the right column to attenuated cells.

Figure 4:
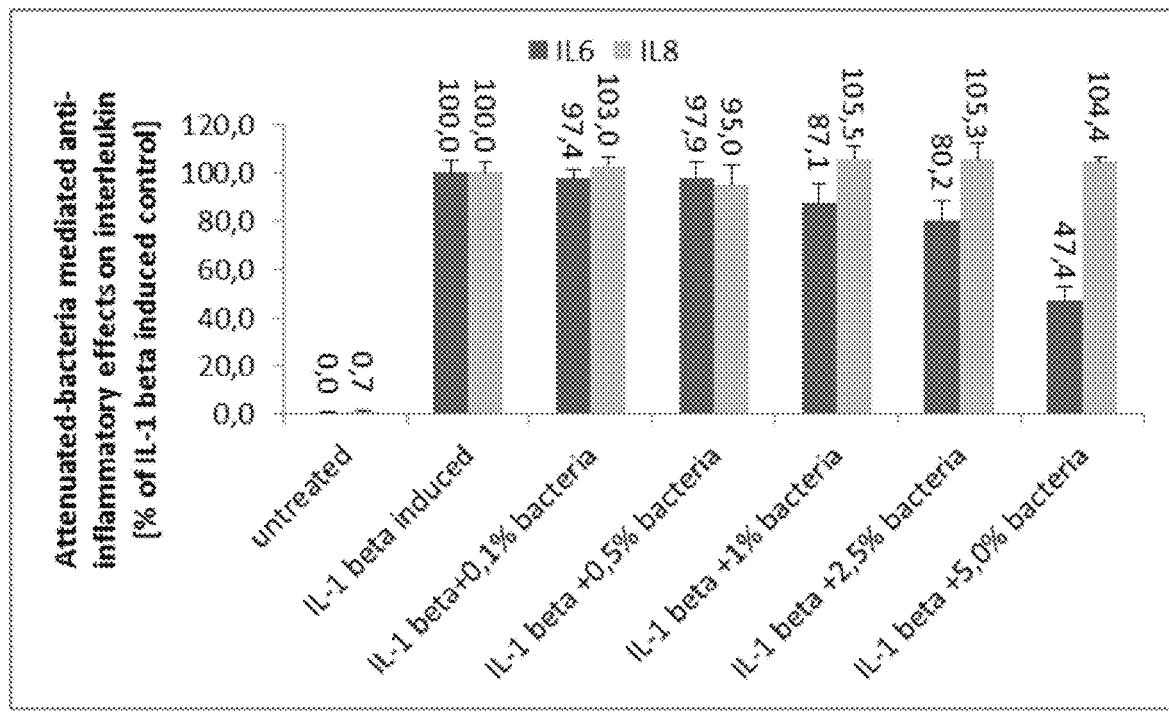
Figure 5A:
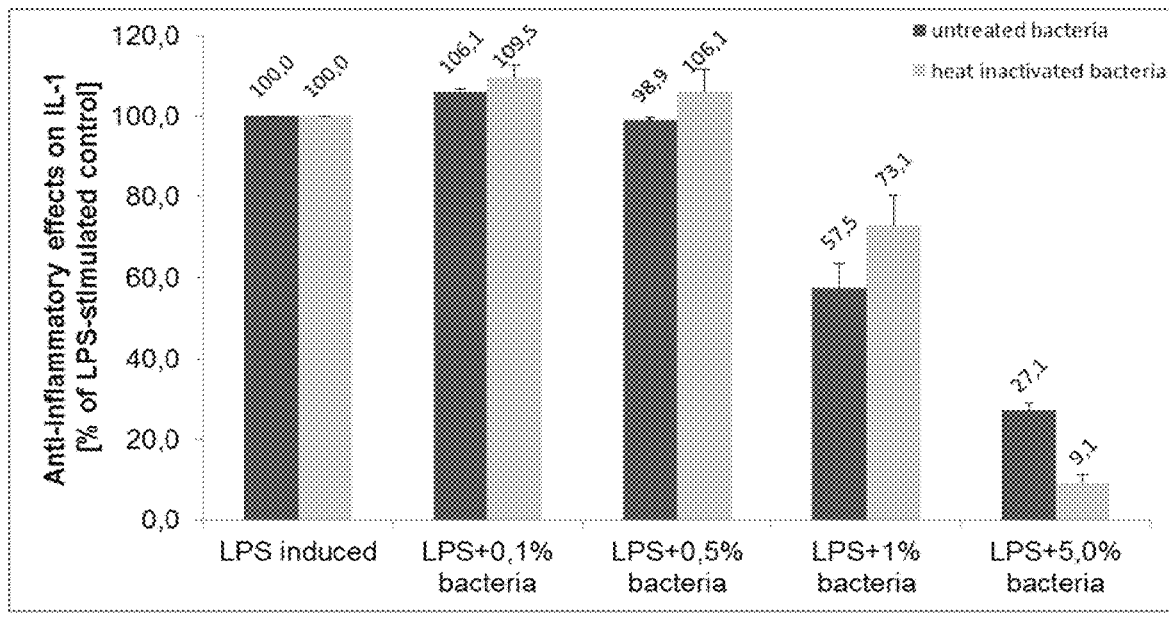
Figure 5B:
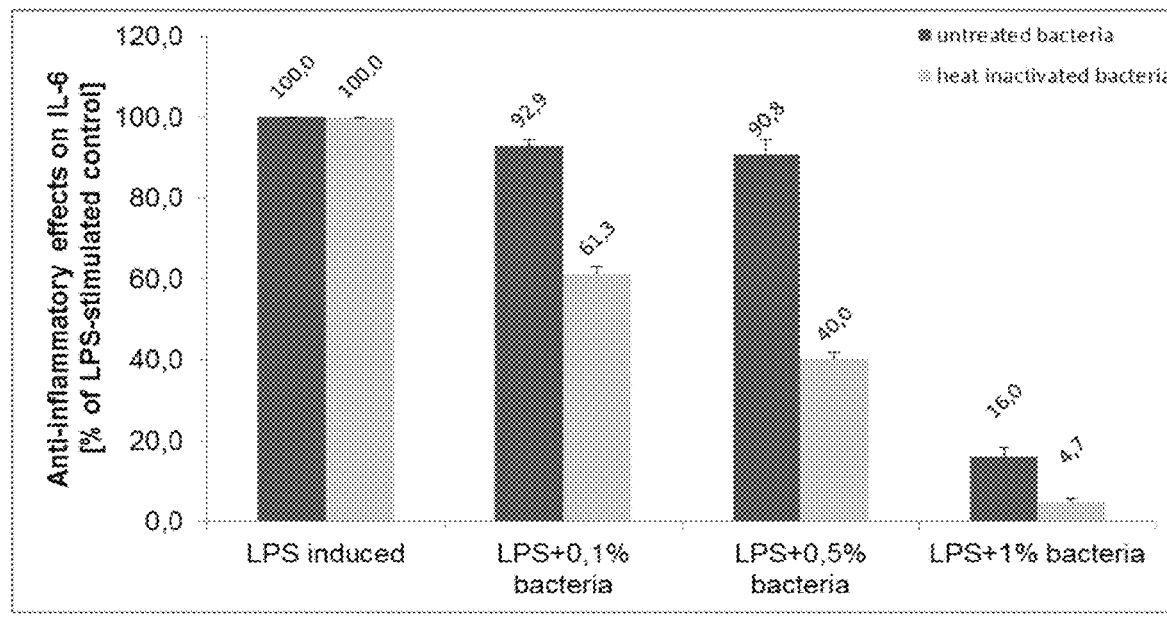
Figure 5C:
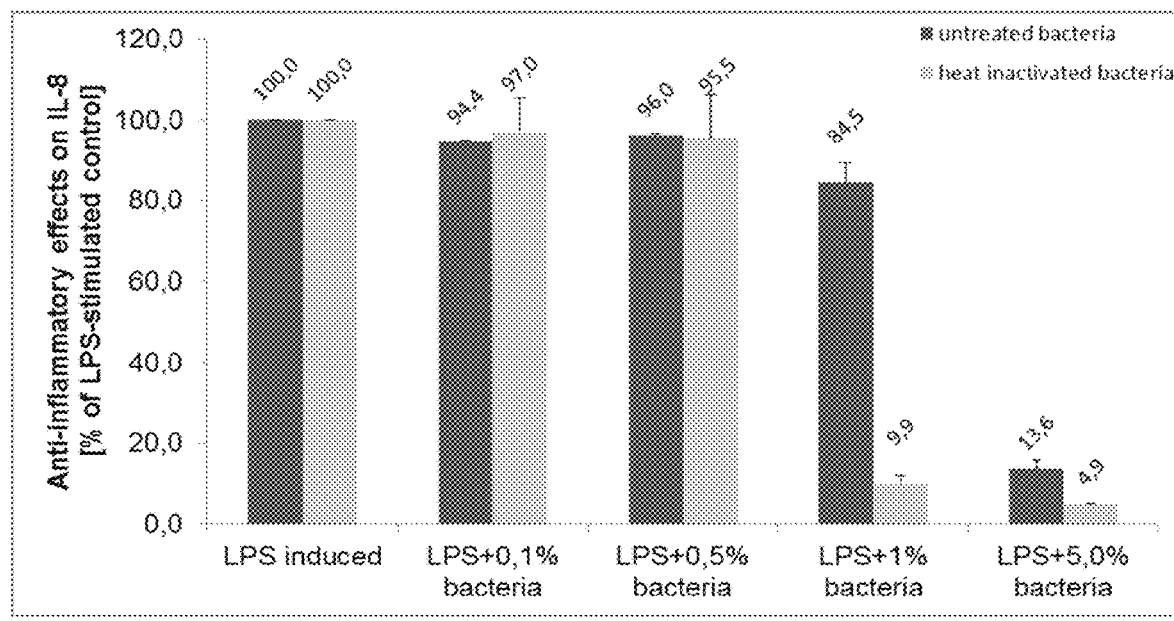
Figure 5D:
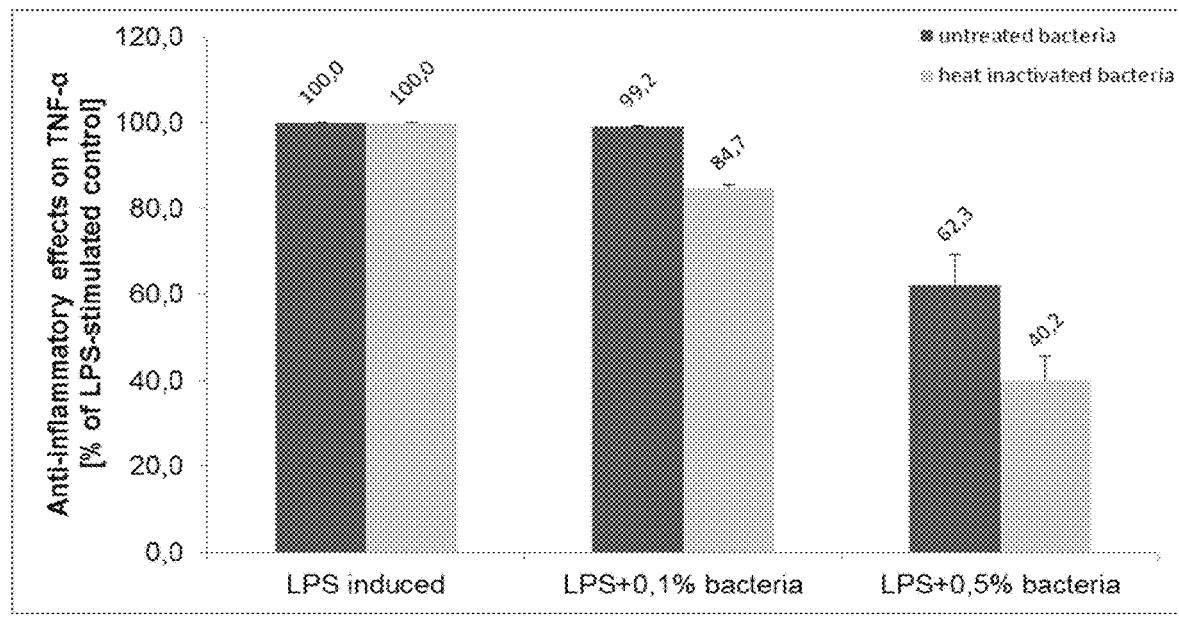
Figure 5E:
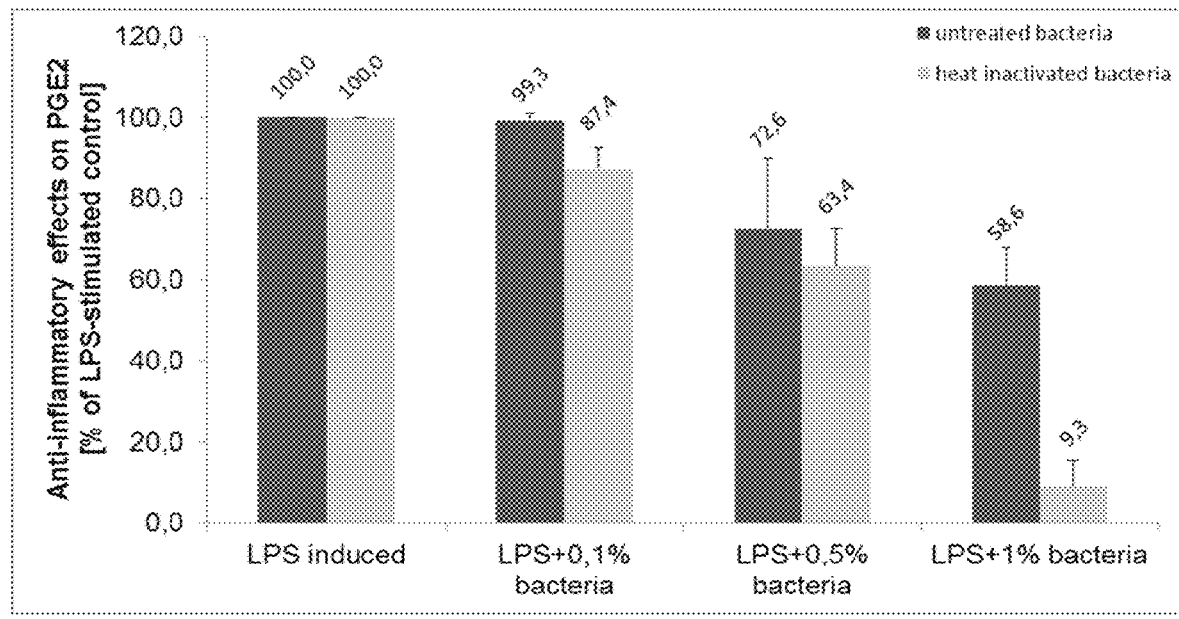
Figure 5F:
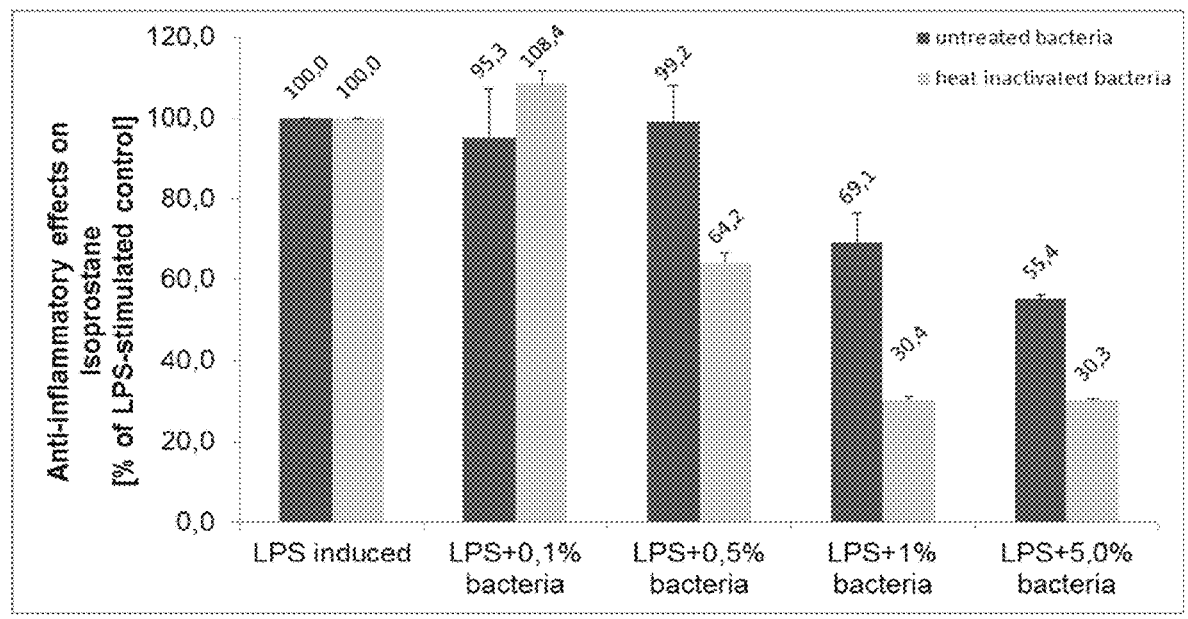
Figure 5G:
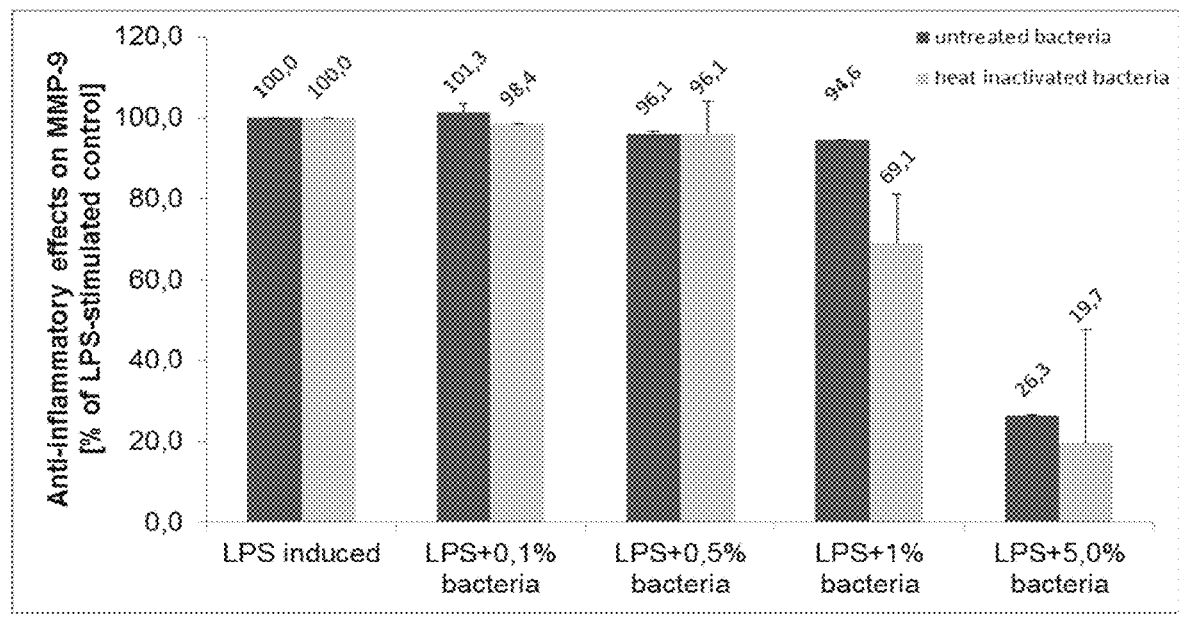
Figure 6A:
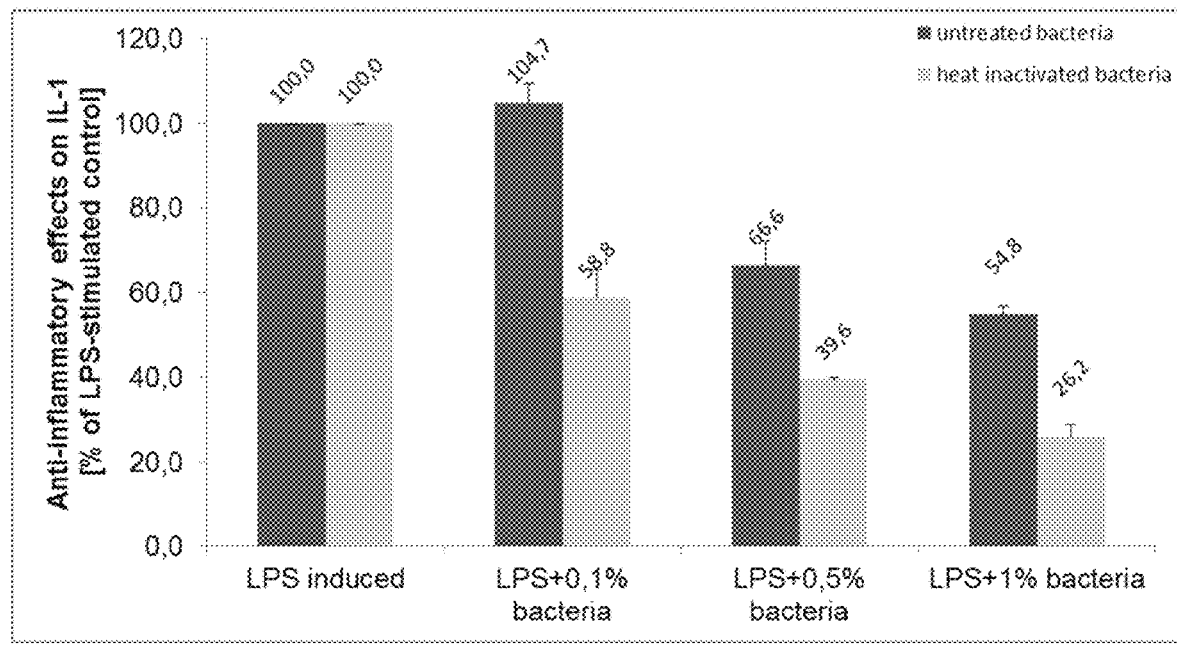
Figure 6B:
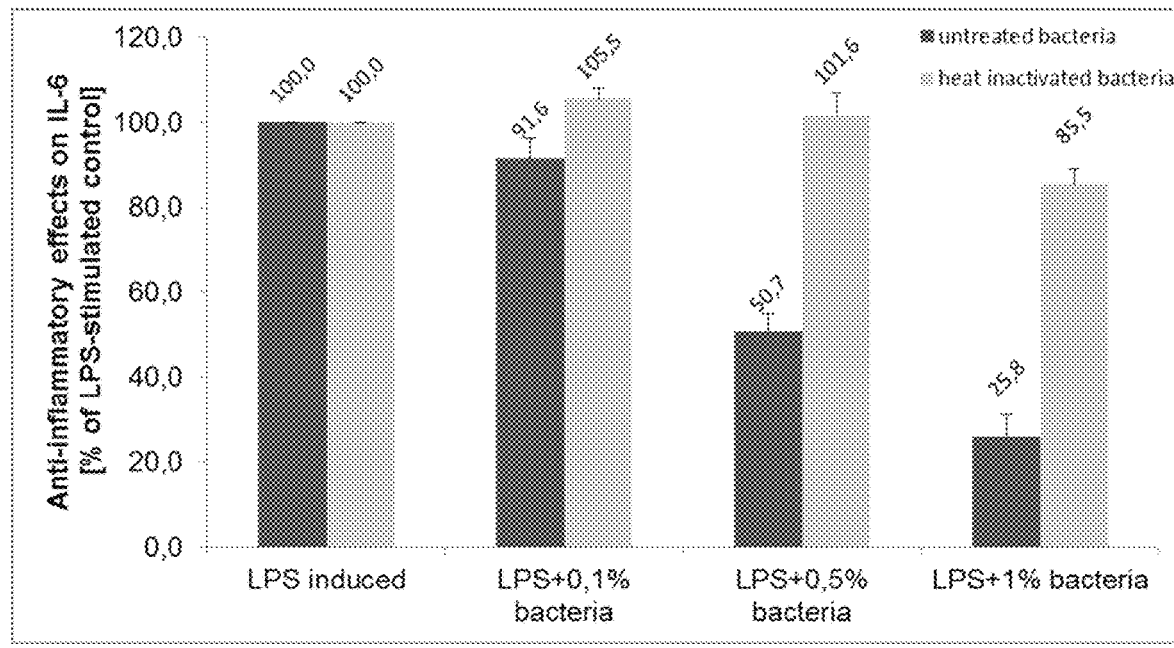
Figure 6C:
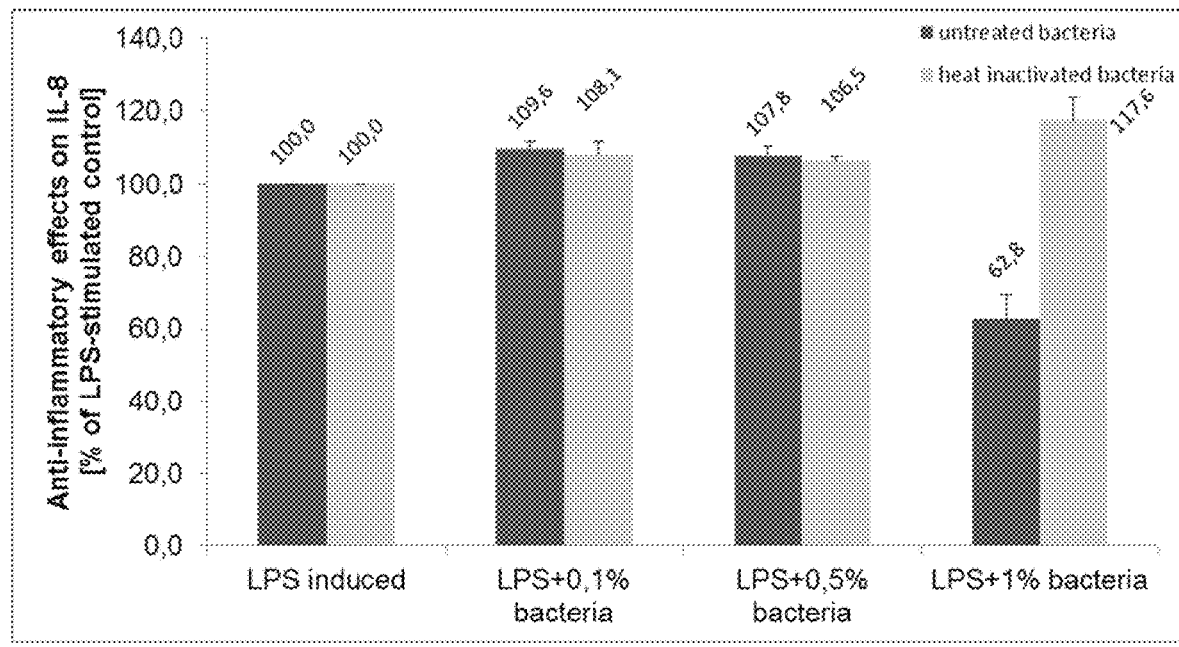
Figure 6D:
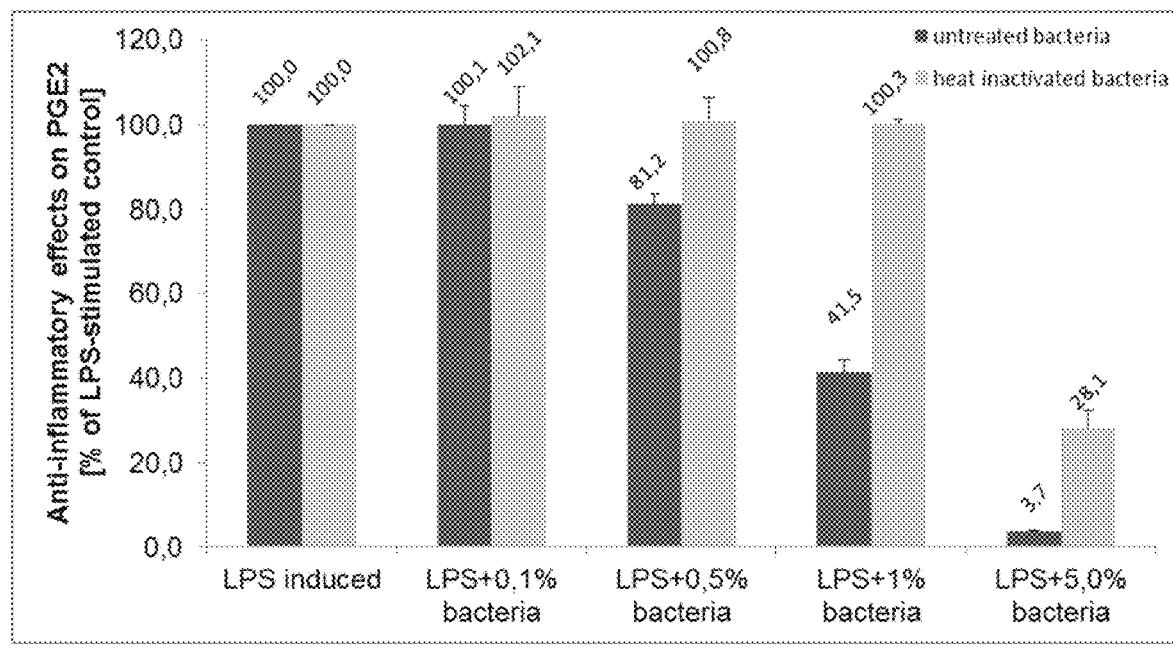
Figure 6E:
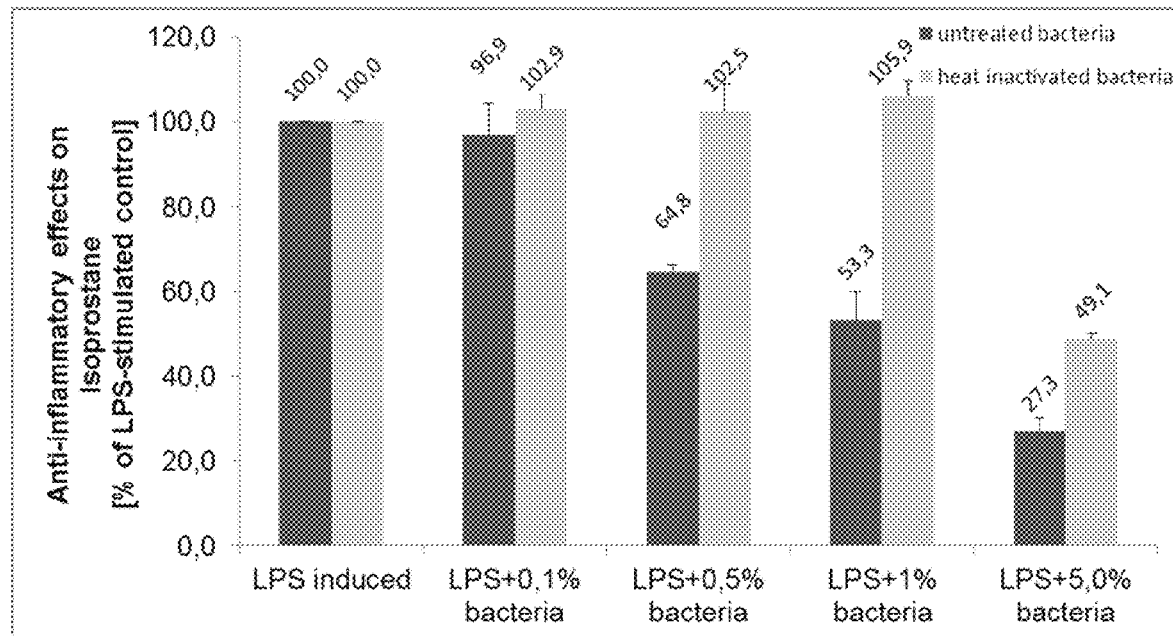
Figure 6F:
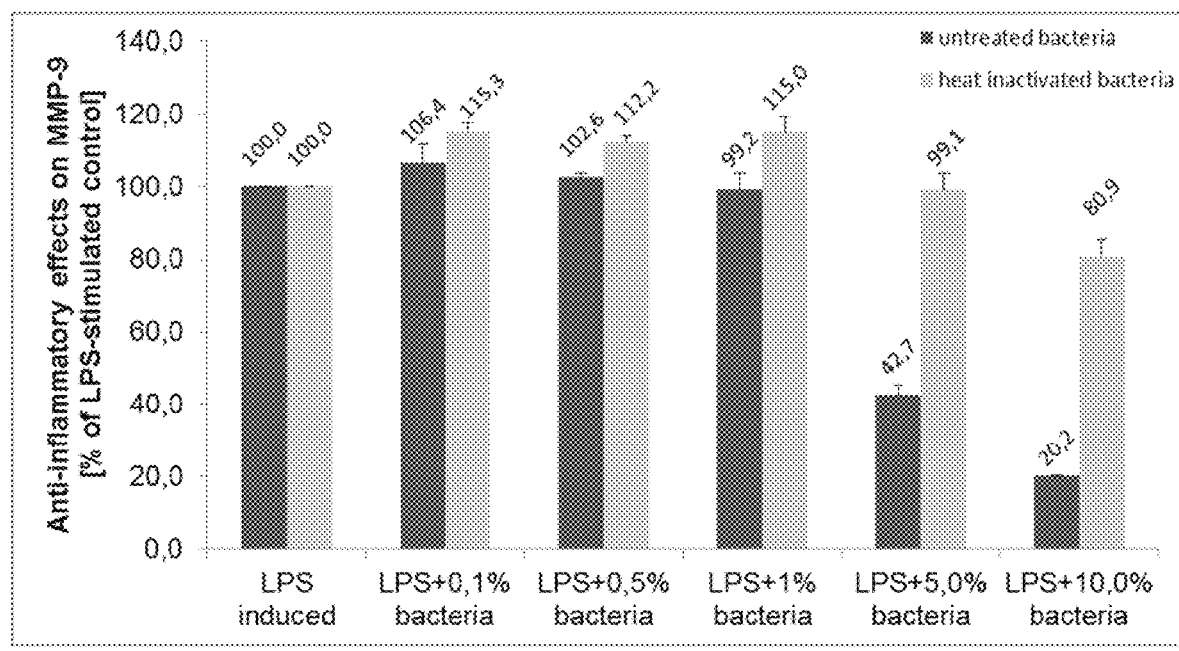
Figure 7A:
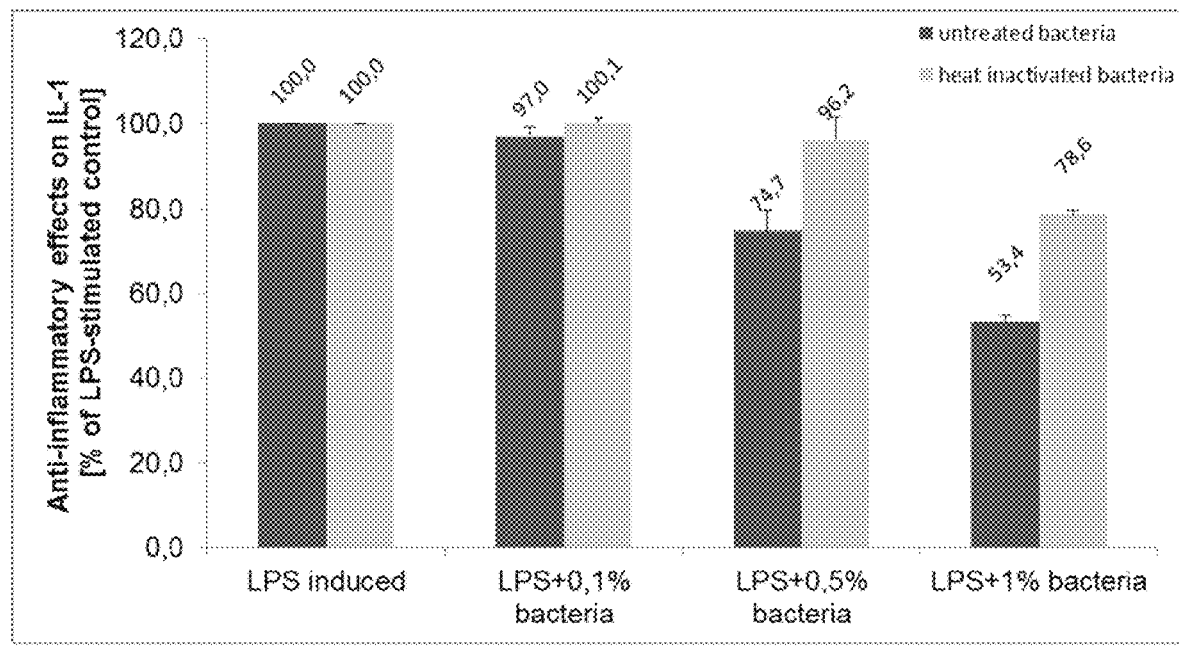
Figure 7B:
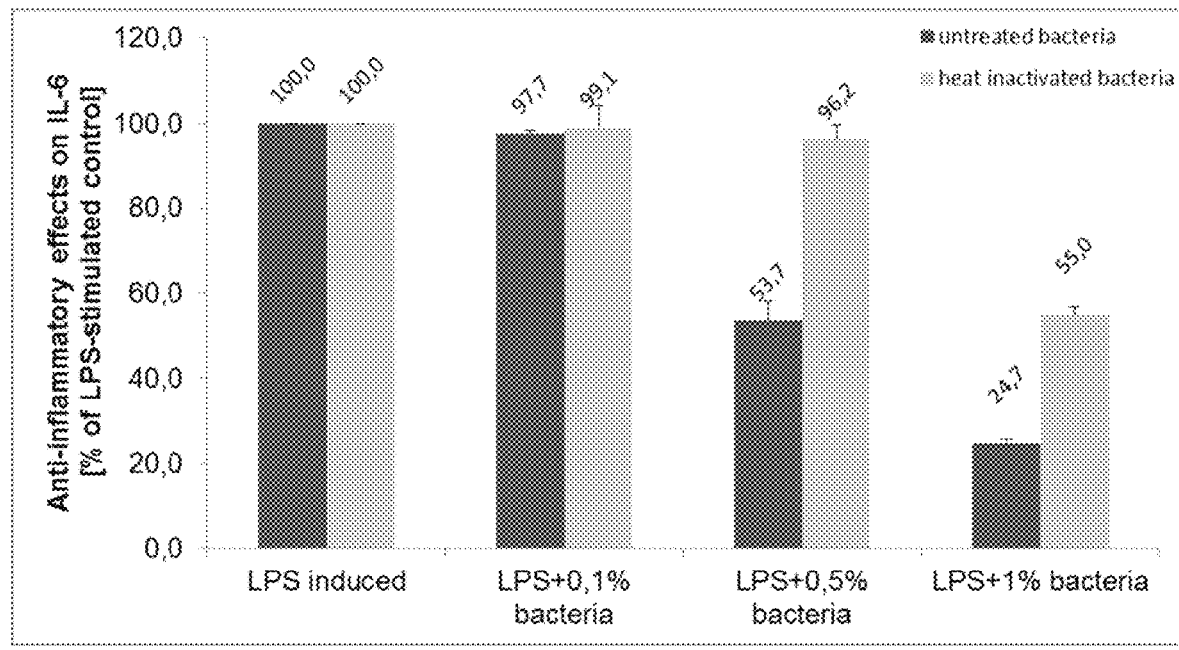
Figure 7C:
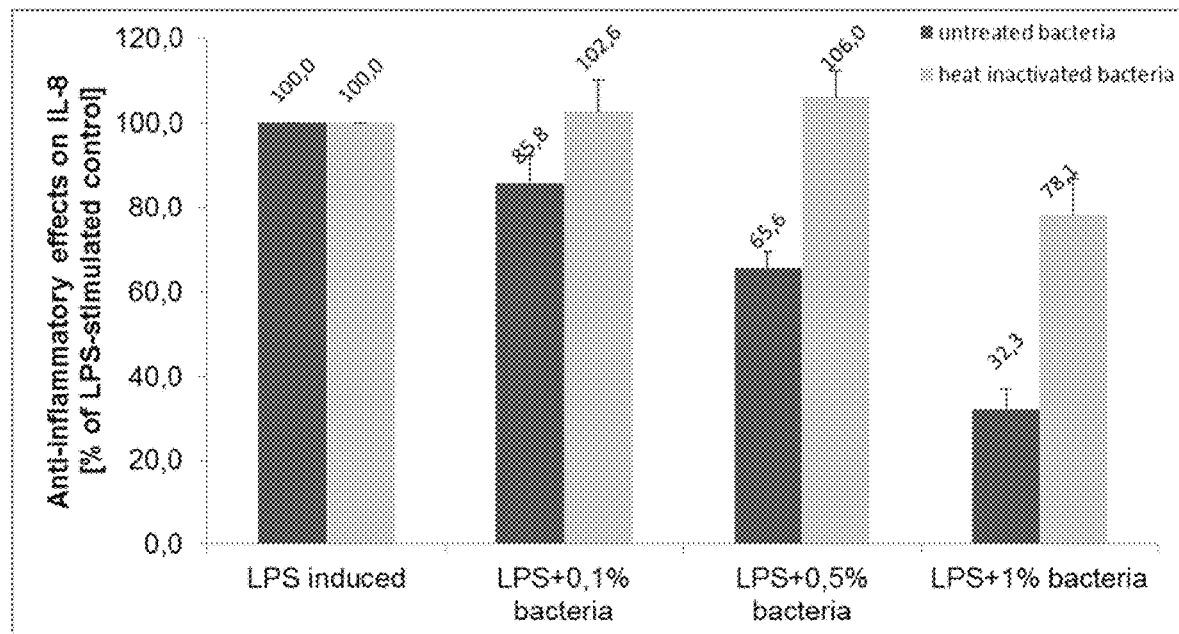
Figure 7D:
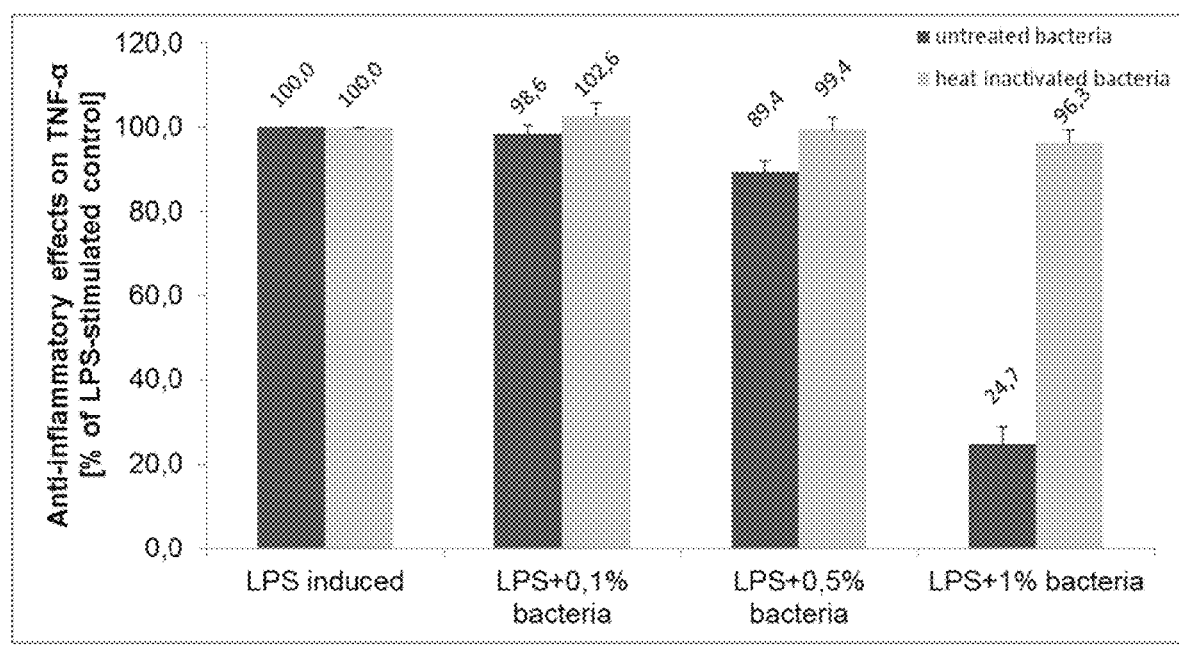
Figure 7E:
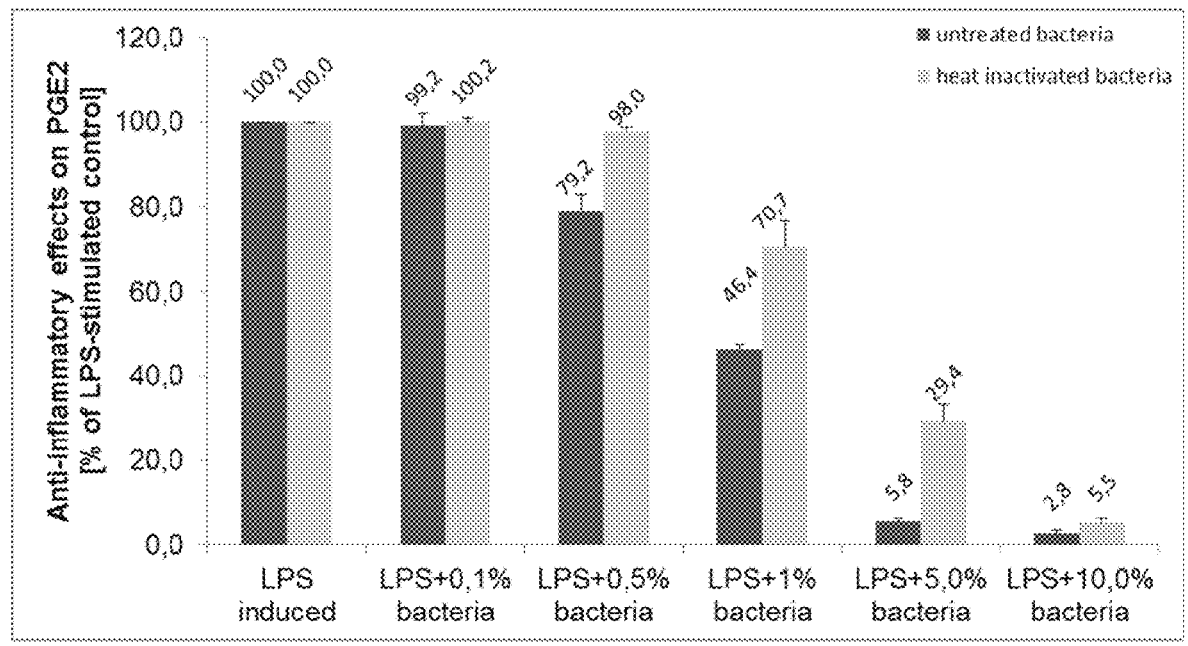
Figure 7F:
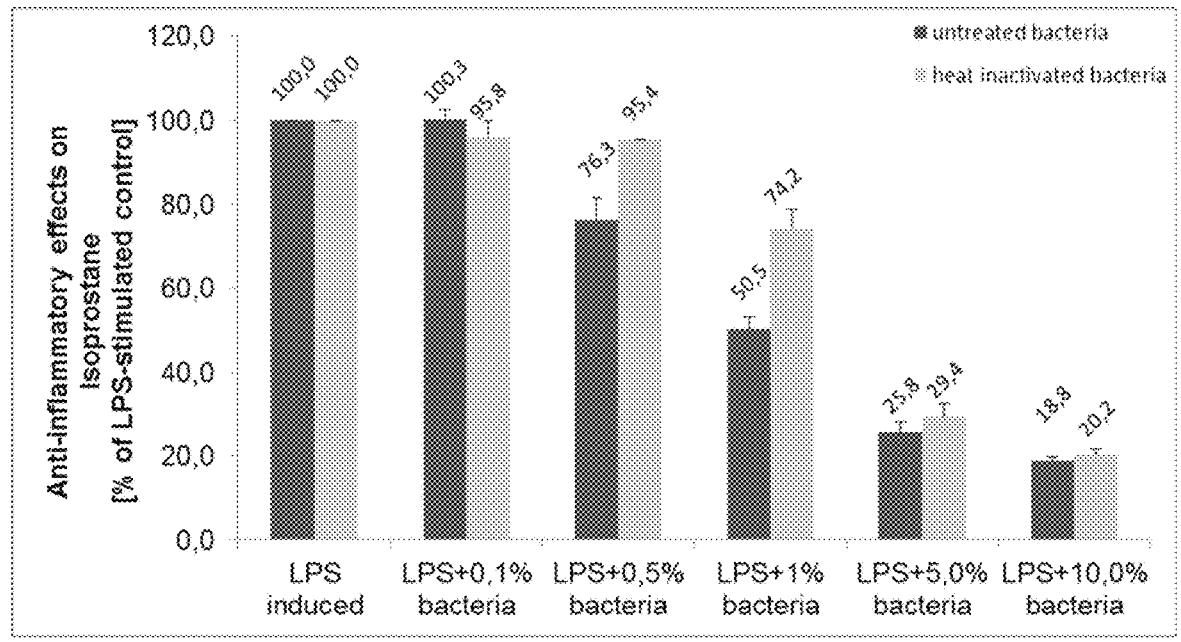
Figure 7G:
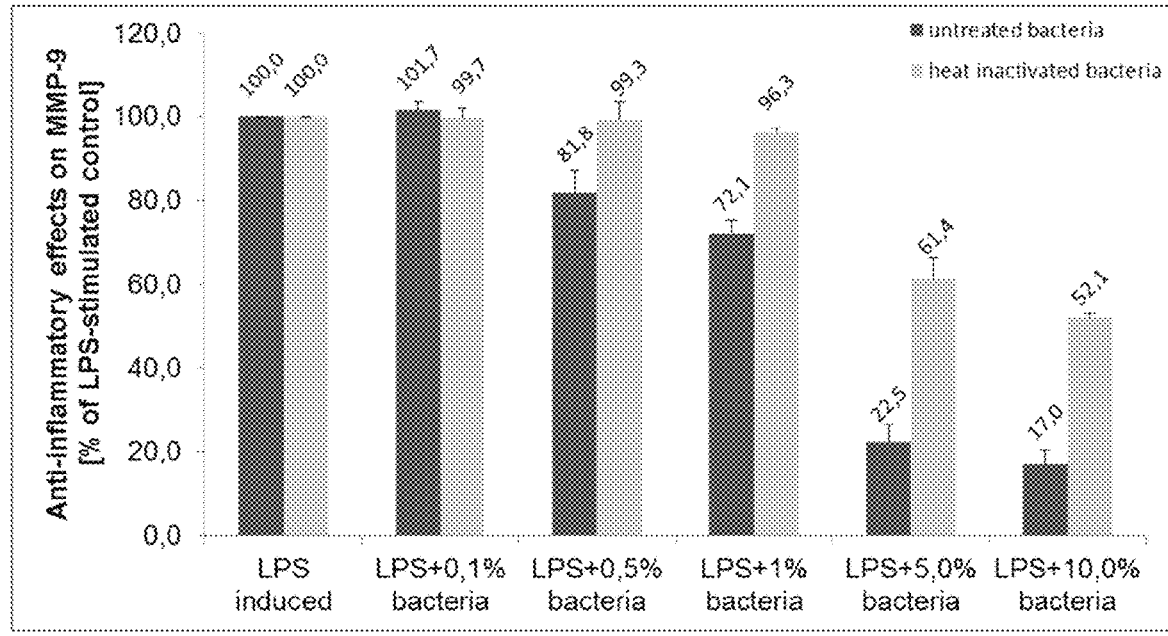

FIG. 4 shows the anti-Inflammatory effects of *Lactobacillus plantarum* GOS 42 (DSM 32131) in attenuated form on interleukin in human gingival fibroblasts. The left column refers to interleukin 6, the right column to interleukin 8.

FIG. 5 shows the anti-inflammatory effects of *Lactobacillus paracasei* (NCIMB 8823) in human primary monocytes on interleukin 1 beta (A), interleukin 6 (B), interleukin 8 (C), tumor necrosis factor alpha (D), prostaglandin E2 (E), isoprostane (F) and metallopeptidase 9 (MMP-9, G). The left column refers to untreated cells, the right column to attenuated cells.

FIG. 6 shows the anti-inflammatory effects of *Lactobacillus plantarum* Heal19 (DSM 15313) in human primary monocytes on interleukin 1 beta (A), interleukin 6 (B), interleukin 8 (C), prostaglandin E2 (D), isoprostane (E) and matrix metallopeptidase 9 (MMP-9, F).

FIG. 7 shows the anti-inflammatory effects of *Lactobacillus delbrueckii* LL-G41 (CCTCC M 2016652) in human primary monocytes on interleukin 1 beta (A), interleukin 6 (B), interleukin 8 (C), tumor necrosis factor alpha(D), prostaglandin E2 (E), isoprostane (F) and matrix metallopeptidase 9 (MMP-9, G). The left column refers to untreated cells, the right column to attenuated cells.

Figure 8:
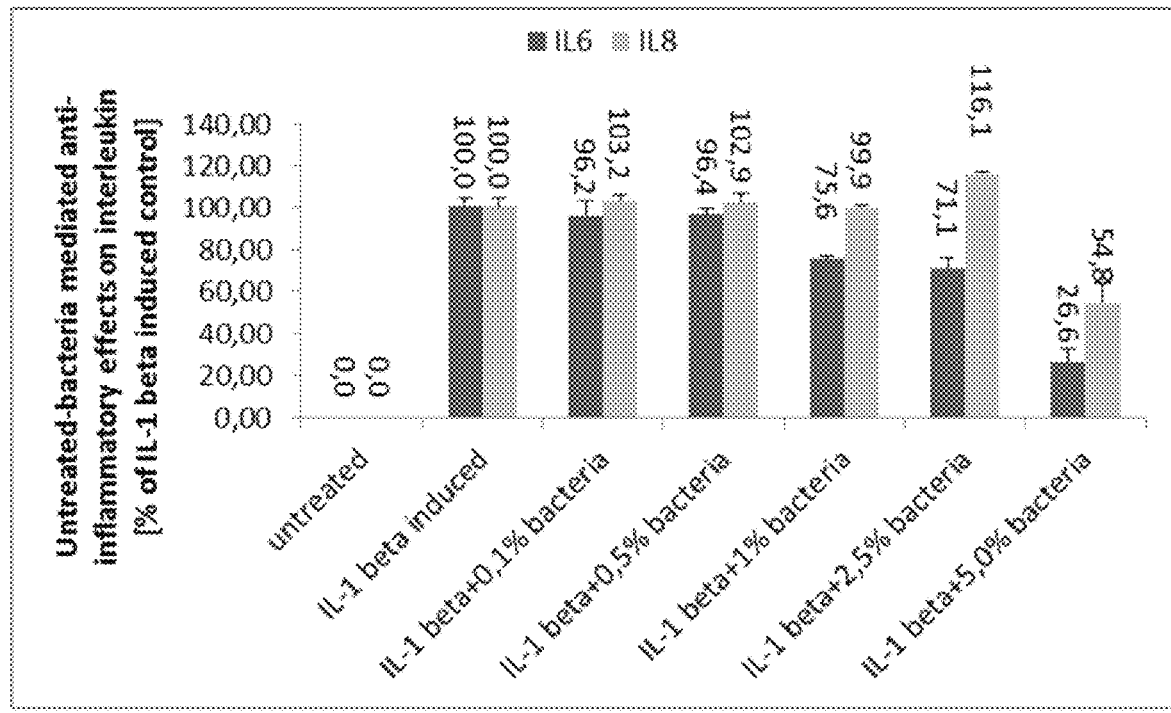

FIG. 8 shows the anti-Inflammatory effects of attenuated *Lactobacillus paracasei* (NCIMB 8823) on interleukin 6 and interleukin 8 in human gingival fibroblasts. The left column refers to interleukin 6, the right column to interleukin 8.

The following examples are added to illustrate the present invention without being intended to limit the scope.

Example 1: Establishing the Cultivation and Handling of Probiotic Strains

The strains of the invention were selected from amongst over 50 candidate probiotic strains tested, including strains of *Bacillus subtilis*, *Bifidobacterium animalis*, *Bifidobacterium bifidum*, *Bifidobacterium longum*, *Bifidobacterium breve*, *Bifidobacterium lactis*, *Lactobacillus acidophilus*, *Lactobacillus casei*, *Lactobacillus* LAFTI, *Lactobacillus plantarum*, *Lactobacillus reuteri*, *Lactobacillus rhamnosus*, *Lactobacillus paracasei*, *Lactobacillus bulgaricus*, *Lactobacillus gasseri*, *Lactobacillus fermentum*, *Lactobacillus brevis*, *Lactobacillus cellobiosus*, *Lactobacillus salivarius*, *Streptococcus thermophilus* and *Lactococcus lactis*.

In order to identify the optimal growth conditions and points of harvest and to determine the colony forming units (CFU) for the probiotic bacteria to be screened, first the log phase and the end of the growth phase were determined.

Bacterial Growth

The frozen (−80° C.) pro-biotic stocks were thawed over-night at 4° C. and 6 ml of sterile 9% NaCl solution added to the 1.2 ml of bacteria at the next morning. The samples were centrifuged (5 min, 5000 rpm), the supernatant discarded, the pellet washed with 8 ml 9% NaCl and again centrifuged for 5 min at 5000 rpm. The pellet was then resuspended in 1.2 ml 9% NaCl and 1 ml of the sample added to 50 ml 37° C. warm media (MRS Bouillon, Carl Roth KG, Karlsruhe) and incubated at 37° C. The incubations were performed in a 50 ml sterile polypropylen tube (Greiner) and probes were harvested at different time points to evaluate the growth curve.

OD-Determination

For determination of OD, 500 µl of the bacterial suspension were removed and diluted in 1 ml MRS Bouillon in a 1.5 ml-PS-cuvette (Brand). OD-determination was performed at 600 nm (ThermoScientific, Helios Epsilon) 1.5 ml MRS Bouillon were used as blanc.

Determination of CFU

For determination of CFU, bacteria were diluted (1:10.000.000, 1:50.000.000 and 1:100.000.000), plated on MRS-agar-plates (MRS Agar, X924, Carl Roth) and incubated for 2 days at 37° C. The grown colonies were then counted and the CFU was calculated.

The bacteria approached the log phase right from the beginning until 7 to 8 hours when they start to reach the plateau phase. The amount of bacteria to be seeded does not change the shape of the curve. 5 hours were chosen as the point at the steepest growing phase to harvest the bacteria in the log phase and 7 hours to harvest them at the end of the log phase.

Example 2: Establishing the Stimulation of Human Monocytes with Probiotics

The stimulation of the monocyte cell cultures with the probiotics was established by using the strains obtained as powder. First, several application forms such as using the grown bacteria (picked from the log-phase), the supernatant of the grown bacterial cultures, direct application of the dissolved powder and powder supernatant were tested. According to the results, the bacteria at the end of the log phase were tested this with two batches of the frozen strain. Instead of using the supernatants, heat inactivation of these two strains was established and compared the inactivated bacteria with the activated bacteria.

Measurement of Cytokine; MMP-9 and PGE2 in Primary Human Monocytes

Human primary monocytes were isolated from buffy coats of healthy human blood donors. Cells were seeded in 24-well-plates for ELISA experiments. Cells were incubated with LPS for 24 h. The probiotics (5 doses) were added 30 min before LPS treatment. After 24 h, supernatants were removed, centrifuged and investigated for IL-1beta, TNFalpha, IL-6, IL-8, MMP-9, isoprostane-8 and $PGE_2$ concentrations in EIAs (PGE2, from AssayDesign, isoprostane, from Cayman) or ELISAs (all cytokines, Immunotools, MMP-9, GE Healthcare) using manufacturer's protocol. Each dose was investigated 2-3 times in two buffy coats from 2 different donors.

First, different types of probiotic lyophilized powder preparations for the stimulation of human monocytes were tested.

The probiotics were harvested and then centrifuged. The cells were dissolved in fresh media and applied to the human monocytes.

The monocytes were then incubated with the probiotics for 30 minutes, then LPS was added and after 24 hours the supernatant removed and use for the determination of the inflammatory parameters.

Example 3: Testing of Heat Inactivated Strains

Establishment of heat inactivation

Heat inactivation was established for two batches. At the end of the bacterial growth log phase, an aliquot of the bacterial suspension was removed, added to a fresh 50 ml tube and incubated for 5 min at 80° C. in a water bath. 5 minutes at 80° C. inactivated the bacteria and thus stopped their growth.

Testing the heat inactivated batches of the strain, it was found that the enhancing effects on IL-1 and TNF were not affected by heat treatment Furthermore, heat activation did not or only slightly affect PGE2 inhibition by both strains.

Example 4: Screening of the Probiotics on Human Monocytes and Effects on NF-kappaB Activation Various probiotic strains were screened in their activated and attenuated (heat-inactivated form) on LPS-induced human primary monocytes (determining IL-1beta, IL-6, IL-8, TNFalpha, PGE2, 8-isoprostane, and MMP-9.

A typical anti-inflammatory pattern of a strain according to Examples 1-4 is given in FIGS. 1 and 3.

The experiments to test effects on NF-kappaB activation induced by TNFin NIH-3T3 fibroblasts were done in a fibroblast cell line that contained stably transfected the Luciferase gene drive by a NF-kappaB dependent promoter. The cells were stimulated with TNF in the presence or absence of the probiotics. After 6 h of stimulation the cells were lysed and the luciferase activity measured in a Luminometer. The most potent strains were selected.

Example 5: Screening of Selected Probiotics on Human Gingival Fibroblasts

Selected strains were applied to human gingival fibroblasts. The fibroblast cultures were maintained as described in the manufacturer's protocol. Prior to stimulation, cells are seeded in 24-well plates for ELISA experiments. Cells were incubated without (unstimulated control) or with IL-1beta for 24 h. The probiotics (5 doses, depending on the outcome of screening assays) are added 30 min before IL-1 treatment. After 24 h, supernatants were removed, centrifuged and investigated for IL-6, IL-8, isoprostane, and PGE2 concentrations in EIA (PGE2, from AssayDesign, isoprostane form Cayman) or ELISA (IL-6, IL-8, Immunotools), using manufacturer's protocol. Each dose was investigated at least 2-3 times. The strains showed some IL-6 inhibiting effects.

An anti-inflammatory pattern of a strain according to Example 5 is given in FIGS. 2 and 4.

Example 6: Probiotic Lozenge or Comprimate

| No | Block | Ingredients | Isomalt Comprimates | | |
|----|-------|-------------|---------|---------------|----------|
|    |       |             | Placebo | Probiotic only | + Flavor |
| 1  | A     | Magnesium Stearate | 1.800% | 1.800% | 1.800% |
| 2  |       | Acesulfam | 0.050% | 0.050% | 0.050% |
| 3  |       | Sucralose | 0.025% | 0.025% | 0.025% |
| 4  |       | Probiotic Material |  | 1.000% | 1.000% |
| 5  |       | Flavor (e.g. 134229 Optamint Peppermint s/d) |  |  | 0.500% |
| 6  | B     | Isomalt | 98.125% | 97.125% | 96.625% |
|    |       | Sum total | 100.00% | 100.00% | 100.00% |

Production Method

Components 1 and 6 are dried in a vacuum compartment drier at 50° C. and a pressure of max. 10 mbar for 16 hours.

All components are weight out exactly components 1, 2, 3, 4 and 5 combined and thoroughly mixed (block A). The probiotic material is applied in lyophilized form having an activity of about $10^5$ to $10^{12}$ colony forming units (CFU) per gram.

Block A is subsequently added to component 6 and mixed thoroughly for 5 minutes.

The powder mixture is pressed into tablets in a tablet press EK0 (Korsch AG, Berlin) at an adjusted pressure of 15-20 kN target parameters:

tablet diameter: 20 mm tablet weight: 2.0 g.

Storage at RT in sealed aluminum sachets. Per 5 lozenges 1 g of desiccant is used for dehumidification (activated by 3 h storage at 105° C. in a vacuum compartment drier).

Example 7: Powder Dentifrice

| No | Block | Ingredients | Toothpowder | | |
|----|-------|-------------|---------|---------------|----------|
|    |       |             | Placebo | Probiotic only | + Flavor |
| 1  | A     | Magnesium Carbonate | 3.00% | 3.00% | 3.00% |
| 2  |       | Sodium Bicarbonate | 2.00% | 2.00% | 2.00% |
| 3  |       | Sodium Fluoride | 0.25% | 0.25% | 0.25% |
| 4  |       | Sodium Saccharin | 0.60% | 0.60% | 0.60% |
| 5  | B     | Probiotic Material |  | 4.00% | 4.00% |

-continued

| No | Block | Ingredients | Toothpowder | | |
|----|-------|-------------|---------|---------------|----------|
|    |       |             | Placebo | Probiotic only | + Flavor |
| 6  |       | Flavor (e.g. 134229 Optamint Peppermint s/d) |  |  | 2.00% |
| 7  | C     | Calcium carbonate | 94.15% | 90.15% | 88.15% |
|    |       | Sum total | 100.00% | 100.00% | 10000% |

Production Method

Component 7 is dried in a vacuum compartment drier at 50° C. and a pressure of max. 10 mbar for 16 hours.

All components are weight out exactly.

Components 1, 2, 3 and 4 are combined and thoroughly mixed together (block A).

Components 5 and 6 are, if necessary, combined and thoroughly mixed (block B). The probiotic material is applied in lyophilized form having an activity of about $10^5$ to $10^{12}$ colony forming units (CFU) per gram.

Blocks A and B are subsequently combined and thoroughly mixed together.

The mixture is added to component 7 and mixed thoroughly for 5 minutes.

The powder mixture is made up into portions of 0.5 g each storage at RT together with 1 g of desiccant per portion (activated by 3 h storage at 105° C. in a vacuum compartment drier) in sealed aluminum sachets.

Example 8: Powder Dentifrice

| No | Block | Ingredients | Toothpaste tablets |
|----|-------|-------------|---------|
| 1  | A     | Magnesium Carbonate | 3.00% |
| 2  |       | Sodium Bicarbonate | 2.00% |
| 3  |       | Sodium Fluoride | 0.25% |
| 4  |       | Sodium Saccharin | 0.60% |
| 5  |       | Sodium Laurylsulphate | 0.50% |
| 6  |       | Magnesium Stearate | 1.00% |
| 7  | B     | Flavor (e.g. 134229 Optamint Peppermint s/d) | 2.00% |
| 8  |       | Probiotic Material | 6.67% |
| 9  | C     | Calcium Carbonate | 17.00% |
| 10 |       | Microcristalline Cellulose | 66.98% |
|    |       | Sum total | 100.00% |

Production Method

Components 6, 9 and 10 are dried in a vacuum compartment drier at 50° C. and a pressure of max. 10 mbar for 16 hours.

All components are weight out exactly.

Components 1, 2, 3, 4, 5 and 6 are combined and thoroughly mixed together (block A).

Components 7 and 8 are combined and thoroughly mixed together (block B). The probiotic material is applied in lyophilized form having an activity of about $10^5$ to $10^{12}$ colony forming units (CFU) per gram.

Blocks A and B are subsequently combined and thoroughly mixed together.

Components 9 and 10 are combined and thoroughly mixed together (block C).

The two mixtures (Block A/B and Block C) are combined and mixed thoroughly for 5 minutes.

The powder mixture is pressed into tablets in a tablet press EK0 (Korsch AG, Berlin) at an adjusted pressure of 15-20 kN target parameters tablet diameter: 9 mm tablet weight: 0.3 g.

Storage at RT in sealed aluminum sachets. Per 3 tablets 1 g of desiccant is used for dehumidification (activated by 3 h storage at 105° C. in a vacuum compartment drier).

Example 9: Chewing Gum

| No | Ingredients | Chewing gum with Vegetable Oil, Probiotics in Flavor | | Chewing gum with Vegetable Oil, Probiotics in Oil | |
|---|---|---|---|---|---|
| 1 | Gum Base (e.g. Geminis T) | 30.00% | Block A | 30.00% | Block A |
| 2 | Isomalt (here: Isomalt ST-PF) | 65.00% | Block B | 65.00% | Block B |
| 3 | Sucralose coated (10% in wax) | 1.00% | | 1.00% | |
| 4 | Deoiled Soy Lecithin (here: Emulpur IP) | 0.30% | | 0.30% | |
| 5 | Vegetable Oil - Triglyceride | 1.60% | Block C | 1.60% | Block C |
| 6 | Probiotic Material | 0.80% | Block D | 0.80% | |
| 7 | Flavor (e.g. 203191 Optamint Peppermint) | 1.30% | | 1.30% | Block D |

Production Method

Component 2 is dried in a vacuum compartment drier at 50° C. and a pressure of max. 10 mbar for 16 hours.

All components are weight out exactly.

Component 1 is tempered to 45-59° C. in a chewing gum lab-kneader with the heating kneaded until a homogenous mass is obtained. The heating is on during the whole mixing process.

Components 2,3 and 4 are added subsequently and kneaded until the mixture is homogenous and no powder is visible anymore.

According to the formula component 6 is either worked into component 5 (block C) or component 7 (block D). The probiotic material is applied in lyophilized form having an activity of about $10^5$ to $10^{12}$ colony forming units (CFU) per gram. The components are mixed until an even suspension is obtained.

First, block C is added to the chewing gum mass and kneaded again until a homogenous mass is obtained.

Last, block D is processed accordingly. After addition the composition has to be kneaded until an even chewing gum mass is obtained.

The mass is taken out of the mixer and is formed into mini-sticks by an embossing roller using the embossing set "slabs".

Storage at RT in sealed aluminum sachets. Per 7 chewing gums 1 g of desiccant is used for dehumidification (activated by 3 h storage at 105° C. in a vacuum compartment drier).

Example 10: Probiotic Beadlets

| components | probiotic beadlets with low load, without aroma, with dye, with gellan gum wt. % | probiotic beadlets with low load, with aroma, with dye, with gellan gum wt. % | probiotic beadlets with high load, without aroma, without dye, without gellan gum, high water content wt. % | probiotic beadlets with high load, without aroma, without dye, without gellan gum, low water content wt. % |
|---|---|---|---|---|
| Alginate | 1.75 | 1.65 | 1.44 | 1.57 |
| Gum arabic | 1.25 | 1.18 | 0.60 | 0.65 |
| Wheat fiber | 1.125 | 1.06 | 0.52 | 0.57 |
| Dye | 0.0125 | 0.018 | — | — |
| Aroma | — | 1.41 | — | — |
| Glycerol | 0.1875 | — | — | — |
| probiotic | 1.125 | 1.35 | 7.20 | 7.83 |
| Gellan Gum | 0.0625 | 0.059 | — | — |
| Water | Add to 100 | Add to 100 | Add to 100 | Add to 100 |
| load | approx. 20% | approx. 20% | approx. 74% | approx. 74% |

Production Method

Production of the calcium chloride bath for precipitation of the alginate beadlets:

A 2% calcium chloride solution is produces from distilled water and calcium chloride. Care has to be taken that the $CaCl_2$ is completely dissolved.

Production of the alginate solution (instead of alginate also pectin or gellan gum may be used):

In a reaction vessel with a stirrer and which is suitable to the batch size, water is provided.

The stirrer is turned on and, while stirring at a high level, the respective amounts of alginate, gum arabic, wheat fiber and probiotic, as well as the optionally required gellan gum are added.

The mixture is heated to 80° C. while stirring and kept at this temperature for 5 minutes—during this step the gel forming components are dissolved.

Afterwards, the heating is turned off and the hot gel solution is further stirred for at least 30 minutes until it is free of lumps.

Subsequently, the solution is cooled by refrigeration to 39-43° C. while stirring.

In a further vessel, the aroma and the dye are provided if required and thoroughly mixed In case no aroma is used, the dye is mixed with glycerol.

When the dye dispersion is mixed homogenously, it is added to the batch vessel with the alginate solution. The mixing vessel is washed several times with approx. 10% of the amount of alginate solution used of water and added to the dispersion.

The alginate dispersion is stirred further for at least 5 minutes.

Subsequently, the batch is stirred for further at least 15 minutes at a low speed to remove potentially present air.

Dripping of the Alginate Solution into the Calcium Chloride Solution for Precipitation of the Beadlets The alginate dispersion is moved to a tightly sealable pressure stable reaction vessel having two outlets. At one outlet pressurized air is applied. The second outlet leads to the nozzles of the dripping unit via a tube.

The reaction vessel is tempered over a heating plate so that the alginate solution reaches a temperature of approx. 45° C. The solution is slightly stirred with a magnet stirrer.

After application of pressure to the reaction vessel, alginate solution is pressed towards the nozzles, which are set to oscillation by an oscillator. By adaption of pressure and the frequency of the oscillator, the size of the resulting drops at the tips of nozzles may be adjusted.

The drops of alginate solution forming at the tips of the nozzles fall into a collection vessel in the form of a funnel in which the calcium chloride solution prepared at the beginning circulates.

The cured alginate beadlets pass with the calcium chloride solution through the funnel and are collected in a sieve, the collected calcium chloride solution is pumped back into the funnel below the dripping unit and thus recycled.

The beadlets are dried in an Aeromatic flowbed-drier at an supply air temperature of 80° C. until an exhaust air temperature of 45° C. is reached.

The invention claimed is:

1. A method of treating gingivitis or periodontitis, comprising introducing a microorganism or mixture comprising two or more microorganisms into the oral cavity of a subject in need thereof, wherein the microorganism(s) is/are selected from the group consisting of *Lactobacillus paracasei* LPc-G110 (CCTCC M 2013691), *Lactobacillus plantarum* GOS 42 (DSM 32131), *Lactobacillus delbrueckii* subsp. *lactis* LL-G41 (CCTCC M 2016652), *Lactobacillus plantarum* Heal19 (DSM 15313), and *Lactobacillus paracasei* NS9 (NCIMB 8823).

2. The method of claim 1, wherein the microorganism(s) is/are (an) attenuated or (a) dead microorganism(s).

3. The method of claim 1, wherein the treating reduces or inhibits release of one or more inflammatory factors selected from the group consisting of interleukin 1 (IL-1), interleukin 6 (IL-6), interleukin 8 (IL-8), tumor necrosis factor (TNF), pros-taglandin E2 (PGE2), isoprostanes, matrix metallopeptidase 9 (MMP9), and NF-$_\kappa$B.

4. The method of claim 1, wherein from $1\times10^3$ to $1\times10^{11}$ colony forming units (CFU) of the microorganism(s) are introducted into the oral cavity.

5. The method of claim 4, wherein from $1\times10^5$ to $1\times10^{10}$ CFU of the microorganism(s) are introduced into the oral cavity.

6. A method of treating gingivitis or periodontitis, comprising introducing into the oral cavity of a person in need thereof, an effective amount of an oral pharmaceutical composition, oral care product, product for nutrition, chewing gum, or lozenge, comprising one or more microorganism(s) selected from the group consisting of *Lactobacillus paracasei* LPc-G110 (CCTCC M 2013691), *Lactobacillus plantarum* GOS 42 (DSM 32131), *Lactobacillus delbrueckii* subsp. *lactis* LL-G41 (CCTCC M 2016652), *Lactobacillus plantarum* Heal19 (DSM 15313), and *Lactobacillus paracasei* NS9 (NCIMB 8823).

* * * * *